(12) United States Patent
Boudreaux et al.

(10) Patent No.: US 11,911,039 B2
(45) Date of Patent: Feb. 27, 2024

(54) CIRCULAR SURGICAL STAPLER HAVING STAPLES WITH EXPANDABLE CROWNS

(71) Applicant: Cilag GmbH International, Zug (CH)

(72) Inventors: Chad P. Boudreaux, Cincinnati, OH (US); Jeffrey L. Aldridge, Lebanon, OH (US); Nicholas M. Morgan, West Chester, OH (US); Michael J. Stokes, Cincinnati, OH (US); Marissa T. Kamenir, Cincinnati, OH (US); John K. Bruce, Morrow, OH (US); John S. Kimsey, Walton, KY (US); Yvan D. Nguetio Tchoumkeu, Blue Ash, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 17/401,451

(22) Filed: Aug. 13, 2021

(65) Prior Publication Data

US 2023/0051659 A1   Feb. 16, 2023

(51) Int. Cl.
*A61B 17/064* (2006.01)
*A61B 17/115* (2006.01)
(Continued)

(52) U.S. Cl.
CPC ...... *A61B 17/1155* (2013.01); *A61B 17/0644* (2013.01); *A61B 2017/07228* (2013.01);
(Continued)

(58) Field of Classification Search
CPC ............ A61B 17/1155; A61B 17/0644; A61B 17/064
(Continued)

(56) References Cited

U.S. PATENT DOCUMENTS

| 2,277,931 A | * | 3/1942 | Moe | ............... F16B 15/08 |
| | | | | 411/475 |
| 4,047,654 A | | 9/1977 | Alvarado | |

(Continued)

FOREIGN PATENT DOCUMENTS

| EP | 1875870 A1 | 1/2008 |
| EP | 2157918 | 3/2010 |

(Continued)

OTHER PUBLICATIONS

U.S. Appl. No. 17/401,391, entitled, "Methods of Forming an Anastomosis Between Organs with an Expandable Pattern," filed Aug. 13, 2021.

(Continued)

*Primary Examiner* — Gloria R Weeks
(74) *Attorney, Agent, or Firm* — Frost Brown Todd LLP

(57) ABSTRACT

A surgical stapler instrument includes a stapling head assembly that receives a plurality of staples. The staples are configured with features that allow the staples to expand after deployment so that an anastomosis created by the instrument can increase in size after forming. In some versions the staples expand automatically after deployment, and in other versions the staples expand in response to tissue forces imparted upon the staples after deployment. In some versions the staples are configured to be deployed in various patterns that promote expandability of the circular staple line.

19 Claims, 21 Drawing Sheets

(51) Int. Cl.
*A61B 17/072* (2006.01)
*A61B 17/11* (2006.01)

(52) U.S. Cl.
CPC ............. *A61B 2017/07264* (2013.01); *A61B 2017/07285* (2013.01); *A61B 17/1114* (2013.01); *A61B 2017/1132* (2013.01)

(58) Field of Classification Search
USPC ...................................................... 606/151
See application file for complete search history.

(56) References Cited

U.S. PATENT DOCUMENTS

| | | | |
|---|---|---|---|
| 4,407,286 A * | 10/1983 | Noiles | A61B 17/0644 227/175.1 |
| 4,505,273 A * | 3/1985 | Braun | A61B 17/0644 606/221 |
| 4,669,647 A * | 6/1987 | Storace | A61B 17/0684 227/19 |
| 4,848,328 A | 7/1989 | Laboureau et al. | |
| 4,874,122 A * | 10/1989 | Froelich | A61B 17/0684 227/19 |
| 4,899,745 A * | 2/1990 | Laboureau | A61B 17/0644 606/151 |
| 5,292,053 A | 3/1994 | Bilotti et al. | |
| 5,309,927 A | 5/1994 | Welch | |
| 5,333,773 A | 8/1994 | Main et al. | |
| 5,342,396 A * | 8/1994 | Cook | A61B 17/0644 227/19 |
| 5,350,104 A | 9/1994 | Main et al. | |
| 5,425,489 A * | 6/1995 | Shichman | A61B 17/0643 606/220 |
| 5,533,661 A | 7/1996 | Main et al. | |
| 5,725,554 A * | 3/1998 | Simon | A61B 17/0684 227/19 |
| 5,732,872 A * | 3/1998 | Bolduc | A61B 17/0644 227/176.1 |
| 5,993,468 A | 11/1999 | Rygaard | |
| 6,352,541 B1 * | 3/2002 | Kienzle | A61B 17/1285 606/143 |
| 6,425,903 B1 * | 7/2002 | Voegele | A61B 90/39 606/220 |
| 6,616,686 B2 | 9/2003 | Coleman et al. | |
| 6,767,356 B2 * | 7/2004 | Kanner | A61B 17/068 606/220 |
| 6,915,937 B2 * | 7/2005 | Lat | B25C 5/00 227/152 |
| 7,056,330 B2 * | 6/2006 | Gayton | A61B 17/0644 606/139 |
| 7,422,138 B2 | 9/2008 | Bilotti et al. | |
| 7,824,426 B2 | 11/2010 | Racenet et al. | |
| 8,143,870 B2 | 3/2012 | Ng et al. | |
| 8,267,301 B2 | 9/2012 | Milliman et al. | |
| 8,328,063 B2 | 12/2012 | Milliman et al. | |
| 8,413,870 B2 | 4/2013 | Pastorelli et al. | |
| 8,613,384 B2 | 12/2013 | Pastorelli et al. | |
| 8,789,738 B2 | 7/2014 | Knodel et al. | |
| 8,801,732 B2 * | 8/2014 | Harris | A61B 17/0684 606/151 |
| 8,910,847 B2 | 12/2014 | Nalagatla et al. | |
| 9,016,541 B2 | 4/2015 | Viola et al. | |
| 9,192,387 B1 | 11/2015 | Holsten et al. | |
| 9,265,500 B2 * | 2/2016 | Sorrentino | A61B 17/068 |
| 9,402,628 B2 | 8/2016 | Beardsley | |
| 9,713,469 B2 | 7/2017 | Leimbach et al. | |
| 9,782,171 B2 | 10/2017 | Viola | |
| 9,848,874 B2 | 12/2017 | Kostrzewski | |
| 9,907,552 B2 | 3/2018 | Measamer et al. | |
| 9,936,949 B2 | 4/2018 | Measamer et al. | |
| 10,080,565 B2 | 9/2018 | Pastorelli et al. | |
| 10,105,134 B2 * | 10/2018 | Biedermann | A61B 17/0682 |
| 10,166,026 B2 * | 1/2019 | Shelton, IV | A61B 17/072 |
| 10,285,705 B2 | 5/2019 | Shelton, IV et al. | |
| 10,639,040 B2 | 5/2020 | Penna et al. | |
| 10,709,452 B2 | 7/2020 | DiNardo et al. | |
| 10,856,867 B2 | 12/2020 | Shelton, IV et al. | |
| 10,925,607 B2 | 2/2021 | Penna et al. | |
| 11,147,559 B2 | 10/2021 | Wise et al. | |
| 11,241,232 B2 | 2/2022 | Guerrera | |
| 11,284,890 B2 | 3/2022 | Nalagatla et al. | |
| 11,291,450 B2 | 4/2022 | Nalagatla et al. | |
| 11,523,821 B2 | 12/2022 | Harris et al. | |
| 11,666,339 B2 * | 6/2023 | Bruce | A61B 17/1114 227/179.1 |
| 2002/0185517 A1 * | 12/2002 | Vresh | A61B 17/115 227/176.1 |
| 2003/0009193 A1 | 1/2003 | Corsaro | |
| 2003/0018236 A1 | 1/2003 | Adams | |
| 2003/0078603 A1 * | 4/2003 | Schaller | A61B 17/06 606/151 |
| 2004/0073237 A1 * | 4/2004 | Leinsing | A61B 17/068 606/151 |
| 2006/0291981 A1 * | 12/2006 | Viola | A61B 17/0644 411/457 |
| 2007/0175963 A1 | 8/2007 | Bilotti et al. | |
| 2008/0082126 A1 * | 4/2008 | Murray | A61B 17/07207 606/221 |
| 2008/0210738 A1 * | 9/2008 | Shelton | A61B 17/0643 227/176.1 |
| 2008/0294179 A1 | 11/2008 | Balbierz et al. | |
| 2009/0001122 A1 | 1/2009 | Prommersberger et al. | |
| 2009/0188964 A1 | 7/2009 | Orlov | |
| 2010/0108740 A1 | 5/2010 | Pastorelli et al. | |
| 2010/0191262 A1 * | 7/2010 | Harris | A61B 17/0682 606/151 |
| 2010/0213240 A1 | 8/2010 | Kostrzewski | |
| 2011/0011916 A1 | 1/2011 | Levine | |
| 2011/0017800 A1 | 1/2011 | Viola | |
| 2012/0080498 A1 * | 4/2012 | Shelton, IV | A61B 17/072 227/180.1 |
| 2012/0083836 A1 * | 4/2012 | Shelton, IV | B25C 5/1686 206/339 |
| 2012/0193395 A1 | 8/2012 | Pastorelli et al. | |
| 2012/0325893 A1 | 12/2012 | Pastorelli et al. | |
| 2013/0168433 A1 | 7/2013 | Kostrzewski | |
| 2013/0172929 A1 * | 7/2013 | Hess | F16B 15/00 227/175.1 |
| 2013/0214027 A1 | 8/2013 | Hessler et al. | |
| 2014/0027493 A1 | 1/2014 | Jankowski | |
| 2014/0158747 A1 | 6/2014 | Measamer et al. | |
| 2015/0083772 A1 | 3/2015 | Miller et al. | |
| 2015/0289872 A1 | 10/2015 | Chen et al. | |
| 2015/0297236 A1 * | 10/2015 | Harris | A61B 17/0684 227/176.1 |
| 2016/0000428 A1 | 1/2016 | Scirica et al. | |
| 2016/0278768 A1 * | 9/2016 | Johnson | A61B 17/068 |
| 2017/0086833 A1 | 3/2017 | Eckert et al. | |
| 2017/0119397 A1 | 5/2017 | Harris et al. | |
| 2017/0231629 A1 | 8/2017 | Stopek et al. | |
| 2017/0281187 A1 | 10/2017 | Shelton, IV et al. | |
| 2017/0281188 A1 | 10/2017 | Shelton, IV et al. | |
| 2017/0281189 A1 | 10/2017 | Nalagatla et al. | |
| 2017/0333064 A1 | 11/2017 | Ebner | |
| 2018/0132849 A1 * | 5/2018 | Miller | A61B 17/07207 |
| 2018/0132854 A1 | 5/2018 | Miller et al. | |
| 2018/0206846 A1 | 7/2018 | Guerrera | |
| 2018/0235616 A1 | 8/2018 | Shelton, IV et al. | |
| 2018/0235635 A1 * | 8/2018 | Rekstad | A61B 17/072 |
| 2018/0242974 A1 | 8/2018 | Guerrera et al. | |
| 2018/0242975 A1 | 8/2018 | Penna et al. | |
| 2018/0325508 A1 | 11/2018 | Aronhalt et al. | |
| 2019/0328390 A1 | 10/2019 | Harris et al. | |
| 2020/0038017 A1 | 2/2020 | Hess et al. | |
| 2020/0054339 A1 | 2/2020 | Scirica et al. | |
| 2020/0205835 A1 | 7/2020 | Nalagatla et al. | |
| 2020/0229814 A1 | 7/2020 | Amariglio et al. | |
| 2020/0281595 A1 | 9/2020 | Wise et al. | |
| 2023/0049242 A1 | 2/2023 | Jones et al. | |
| 2023/0102965 A1 | 3/2023 | Wise et al. | |

(56) References Cited

U.S. PATENT DOCUMENTS

FOREIGN PATENT DOCUMENTS

| EP | 2649949 | A1 | 10/2013 |
| EP | 3225176 | A1 | 10/2017 |
| EP | 3225179 | A1 | 10/2017 |
| EP | 3245958 | A1 | 11/2017 |
| EP | 3130292 | B1 | 8/2018 |
| EP | 3173030 | B1 | 10/2019 |
| EP | 3643252 | A1 | 4/2020 |
| WO | WO 2001/054594 | A1 | 8/2001 |
| WO | WO 2002/009595 | A1 | 2/2002 |
| WO | WO 2005/115254 | A2 | 12/2005 |
| WO | WO 2008/141288 | A1 | 11/2008 |
| WO | WO 2020/249487 | A1 | 12/2020 |

OTHER PUBLICATIONS

U.S. Appl. No. 17/401,428, entitled, "Staple Forming Features for Circular Surgical Stapler," filed Aug. 13, 2021.

U.S. Appl. No. 17/401,430, entitled, "Non-Circular End Effector Features for Surgical Stapler," filed Aug. 13, 2021.

U.S. Appl. No. 17/401,439, entitled, "Circular Surgical Stapler End Effector Having Staple Line Alignment Feature," filed Aug. 13, 2021.

U.S. Appl. No. 17/401,444, entitled, "Circular Surgical Stapler for Forming Pattern of Non-Tangential Staples," filed Aug. 13, 2021.

U.S. Appl. No. 17/401,460, entitled, "Circular Surgical Stapler for Forming Cross-Pattern of Staples," filed Aug. 13, 2021.

International Search Report and Written Opinion dated Nov. 14, 2022, for International Application No. PCT/IB2022/057444, 12 pages.

International Search Report and Written Opinion dated Jan. 27, 2023, for International Application No. PCT/IB2022/057446, 19 pages.

International Search Report and Written Opinion dated Nov. 23, 2022, for International Application No. PCT/IB2022/057449, 15 pages.

International Search Report and Written Opinion dated Jan. 25, 2023, for International Application No. PCT/IB2022/057442, 20 pages.

International Search Report and Written Opinion dated Nov. 14, 2022, for International Application No. PCT/IB2022/057443, 12 pages.

International Search Report and Written Opinion dated Nov. 24, 2022, for International Application No. PCT/IB2022/057451, 13 pages.

\* cited by examiner

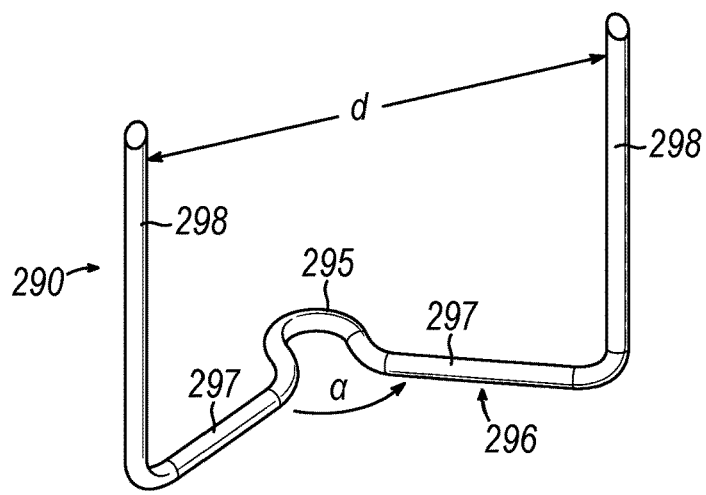
FIG. 13
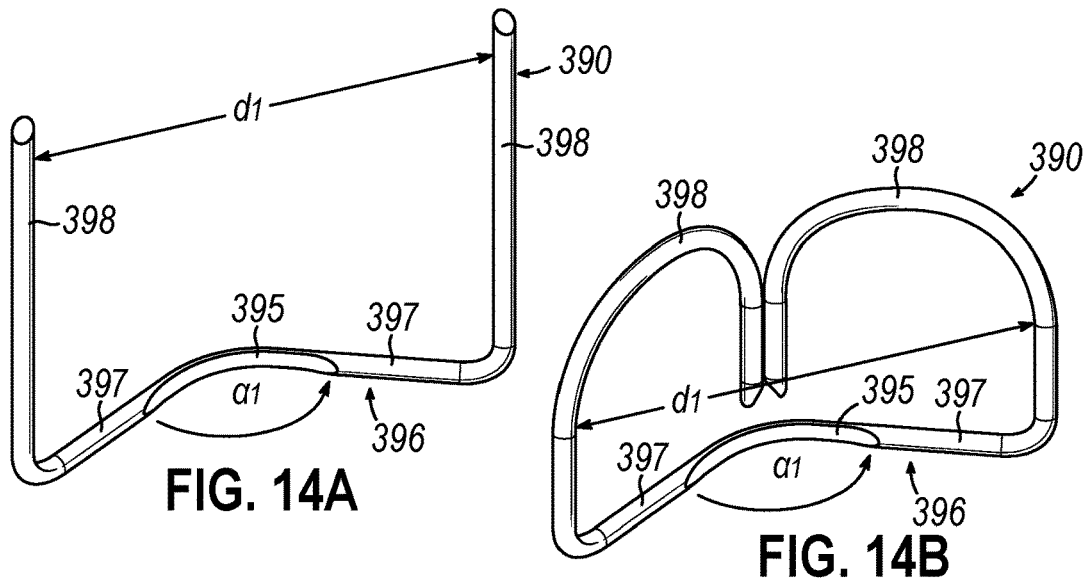
FIG. 14A
FIG. 14B
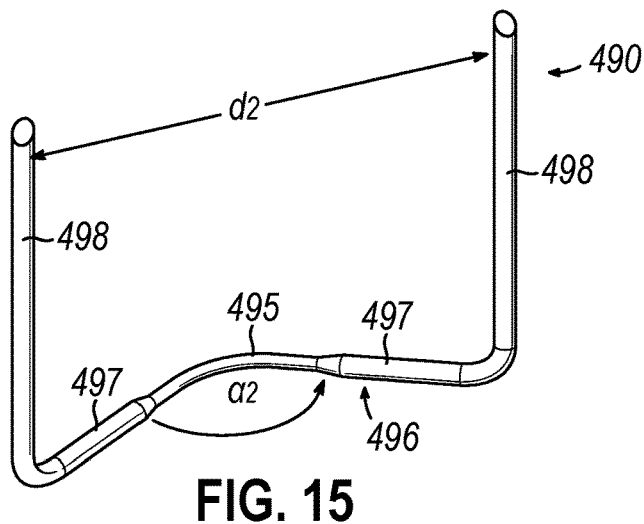
FIG. 15

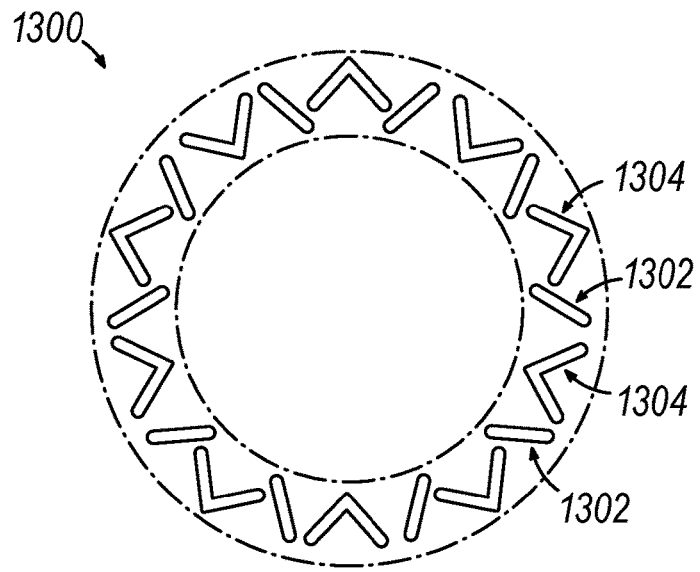
FIG. 20E
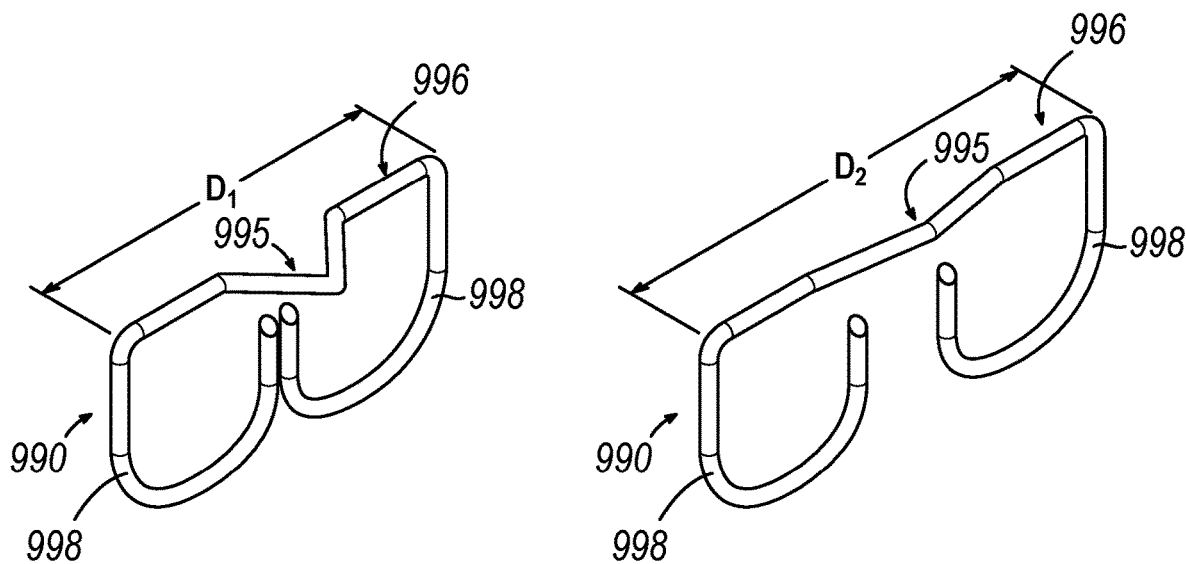
FIG. 21A     FIG. 21B

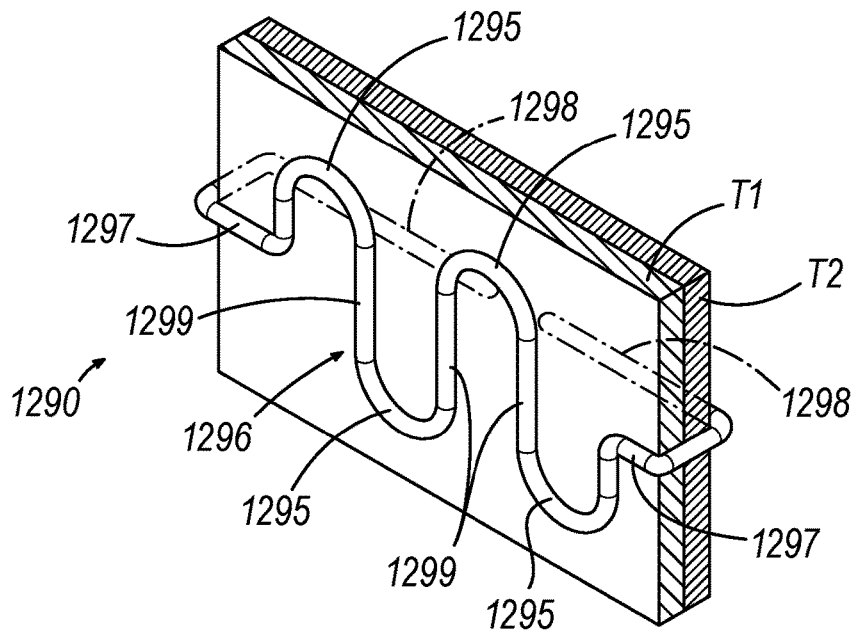
FIG. 24
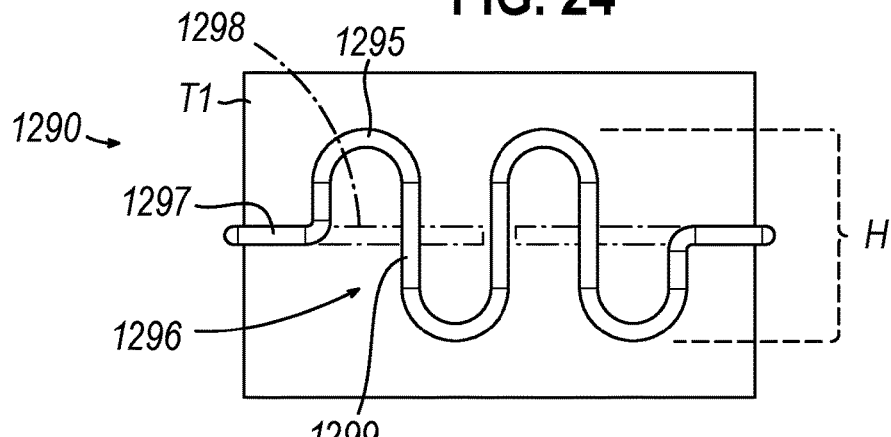
FIG. 25
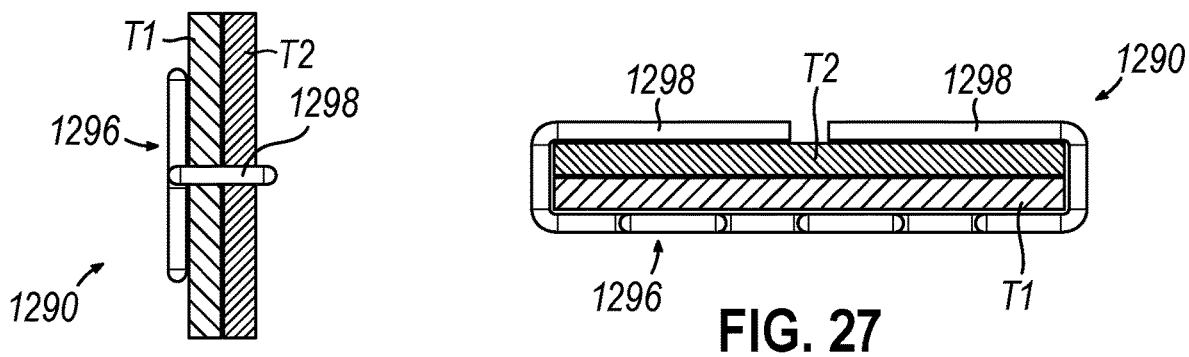
FIG. 26
FIG. 27

FIG. 28 ced CIRCULAR SURGICAL STAPLER HAVING
STAPLES WITH EXPANDABLE CROWNS

BACKGROUND

A circular surgical stapler may be used to form an anastomosis between two organ portions of a patient's digestive tract. Examples of circular surgical staplers are described in U.S. Pat. No. 5,292,053, entitled "Surgical Anastomosis Stapling Instrument," issued Mar. 8, 1994; U.S. Pat. No. 5,333,773, entitled "Surgical Anastomosis Stapling Instrument," issued Aug. 2, 1994; U.S. Pat. No. 5,350,104, entitled "Surgical Anastomosis Stapling Instrument," issued Sep. 27, 1994; and U.S. Pat. No. 5,533,661, entitled "Surgical Anastomosis Stapling Instrument," issued Jul. 9, 1996; and U.S. Pat. No. 8,910,847, entitled "Low Cost Anvil Assembly for a Circular Stapler," issued Dec. 16, 2014. The disclosure of each of the above-cited U.S. Patents is incorporated by reference herein.

Some circular staplers may include a motorized actuation mechanism. Examples of circular staplers with motorized actuation mechanisms are described in U.S. Pub. No. 2015/0083772, entitled "Surgical Stapler with Rotary Cam Drive and Return," published Mar. 26, 2015, now abandoned; U.S. Pat. No. 9,936,949, entitled "Surgical Stapling Instrument with Drive Assembly Having Toggle Features," issued Apr. 10, 2018; U.S. Pat. No. 9,907,552, entitled "Control Features for Motorized Surgical Stapling Instrument," issued Mar. 6, 2018; U.S. Pat. No. 9,713,469, entitled "Surgical Stapler with Rotary Cam Drive," issued Jul. 25, 2017; U.S. Pub. No. 2018/0132849, entitled "Staple Forming Pocket Configurations for Circular Surgical Stapler Anvil," published May 17, 2018; and U.S. Pat. No. 10,709,452, entitled "Methods and Systems for Performing Circular Stapling," issued Jul. 14, 2020. The disclosure of each of the above-cited U.S. Patent Publications and U.S. Patents is incorporated by reference herein.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 13 depicts a perspective view of an exemplary staple having a "V" shape and a spring feature;

FIG. 14A depicts a perspective view of an exemplary staple having a "V" shape and a notch feature;

FIG. 14B depicts a perspective view of the staple of FIG. 14A, but shown in the formed state;

FIG. 15 depicts a perspective view of an exemplary staple having a "V" shape and reduced diameter feature;

FIGS. 20A-20E depicts top views of exemplary staple patterns;

FIG. 21A depicts a perspective view of an exemplary staple having a crown with an expandable angled bend, shown in a relaxed state;

FIG. 21B depicts a perspective view of the staple of FIG. 21A, shown in an expanded state;

FIG. 24 depicts a perspective view of another exemplary staple fastening two tissues together, with the staple having a crown with curved portions;

FIG. 25 depicts a bottom view of the staple and tissues of FIG. 24;

FIG. 26 depicts a side view of the staple and tissues of FIG. 24;

FIG. 27 depicts a front view of the staple and tissues of FIG. 24;

FIG. 28 depicts bottom views of exemplary staples with curved crown portions in various states as well as a top view of exemplary staple patters associated with each of the exemplary staples;

Figure 1:
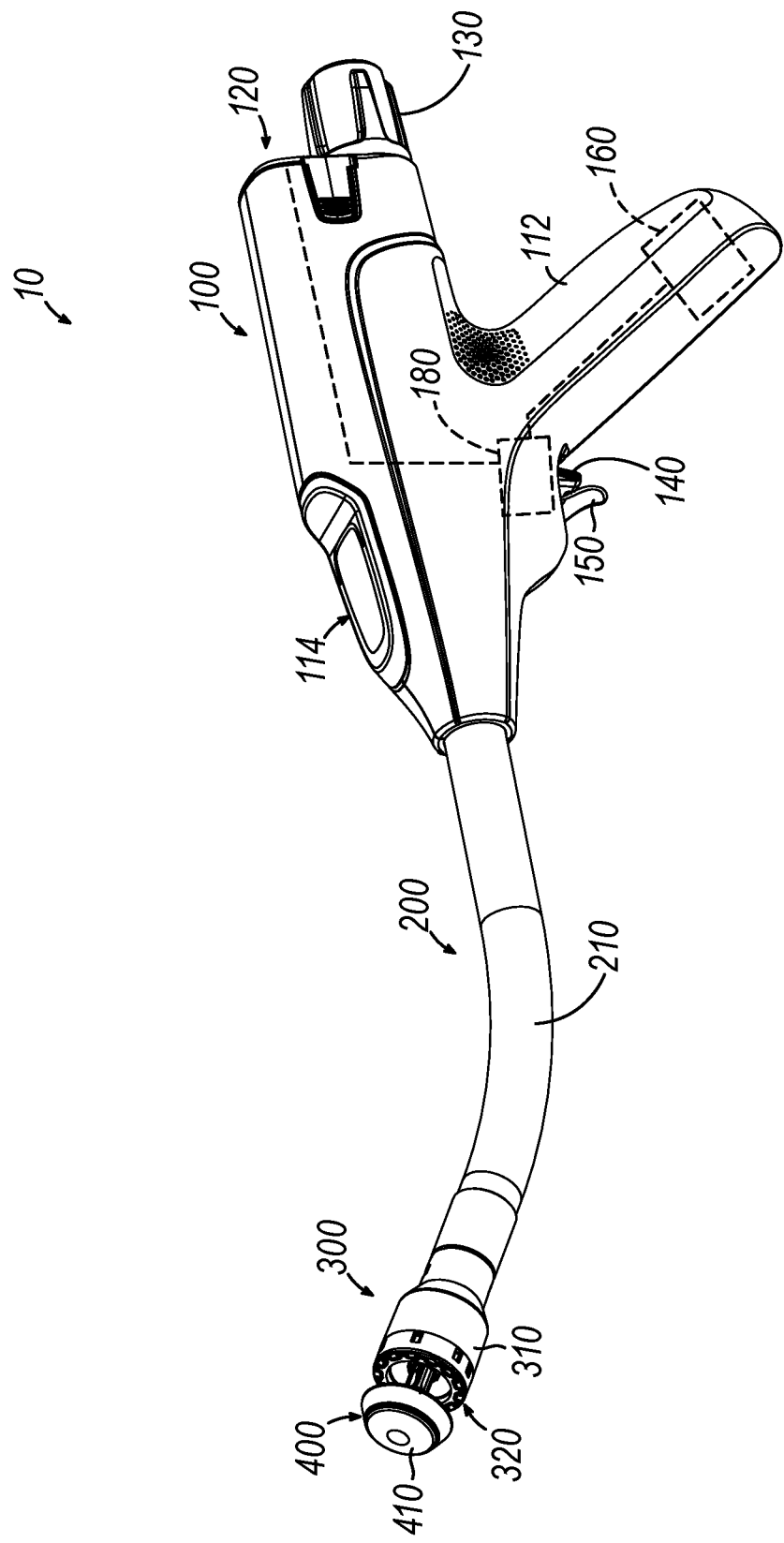
FIG. 1 depicts a perspective view of an exemplary circular surgical stapler that includes a handle assembly, a shaft assembly, and an end effector having a stapling head assembly and an anvil.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

For clarity of disclosure, the terms "proximal" and "distal" are defined herein relative to a surgeon, or other operator, grasping a surgical instrument having a distal surgical end effector. The term "proximal" refers to the position of an element arranged closer to the surgeon, and the term "distal" refers to the position of an element arranged closer to the surgical end effector of the surgical instrument and further away from the surgeon. Moreover, to the extent that spatial terms such as "top," "bottom," "upper," "lower," "vertical," "horizontal," or the like are used herein with reference to the drawings, it will be appreciated that such terms are used for exemplary description purposes only and are not intended to be limiting or absolute. In that regard, it will be understood that surgical instruments such as those disclosed herein may be used in a variety of orientations and positions not limited to those shown and described herein.

Furthermore, the terms "about," "approximately," and the like as used herein in connection with any numerical values or ranges of values are intended to encompass the exact value(s) referenced as well as a suitable tolerance that enables the referenced feature or combination of features to function for the intended purpose described herein.

I. Overview of Exemplary Circular Surgical Stapling Instrument

Figure 2:
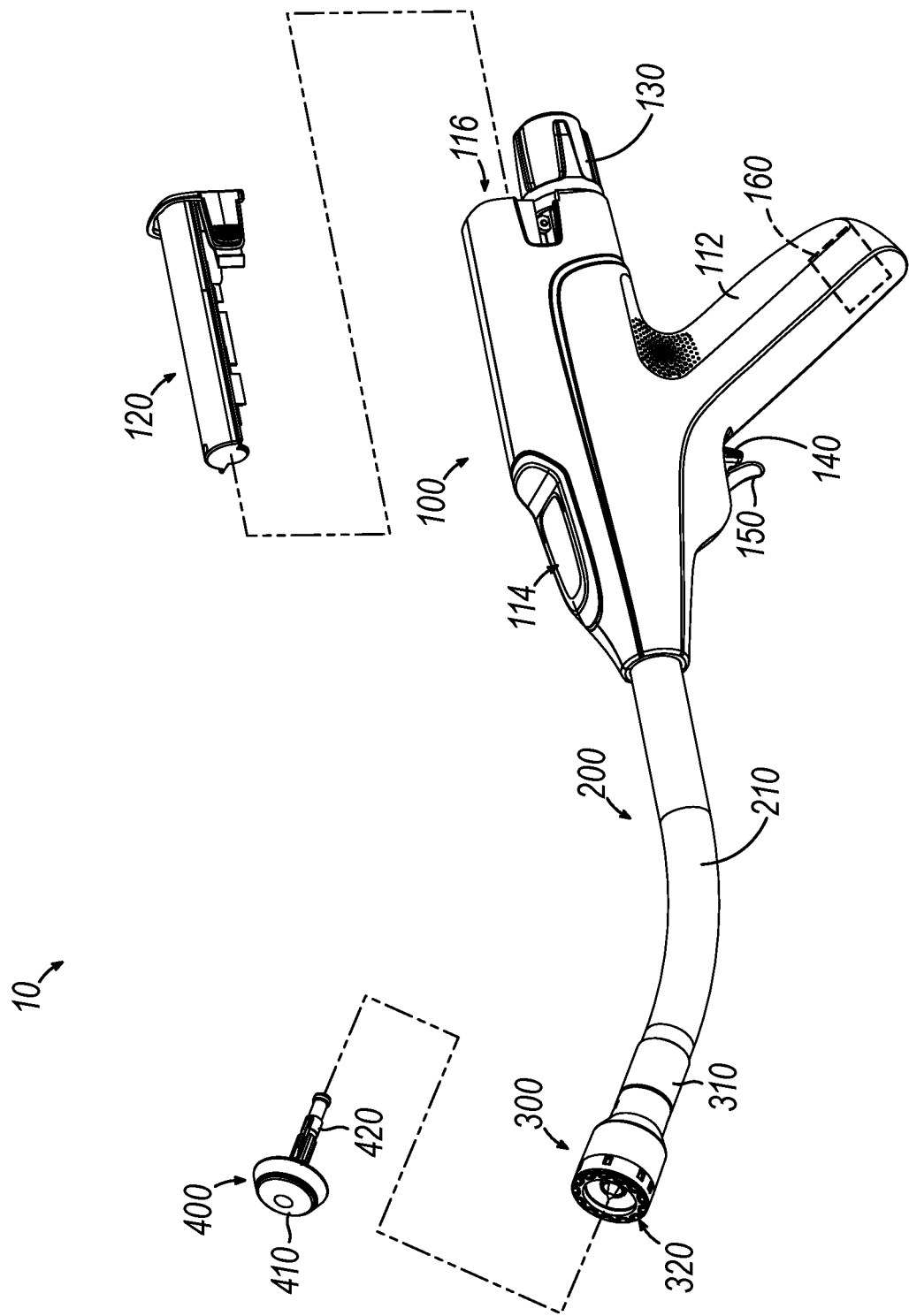
FIG. 2 depicts a perspective view of the circular stapler of FIG. 1, with a battery pack removed from the handle assembly and the anvil separated from the stapling head assembly.

FIGS. 1-2 depict an exemplary circular surgical stapling instrument (10) that may be used to provide an end-to-end, side-to-side, or end-to-side anastomosis between two sections of an anatomical lumen such as a portion of a patient's digestive tract. Instrument (10) of this example includes a body assembly in the form of a handle assembly (100), a shaft assembly (200) extending distally from handle assembly (100), a stapling head assembly (300) at a distal end of shaft assembly (200), and an anvil (400) configured to releasably couple and cooperate with stapling head assembly (300) to clamp, staple, and cut tissue. Instrument (10) further includes a removable battery pack (120) operable to provide electrical power to a motor (160) housed within handle assembly (100), as will be described in greater detail below.

As shown in FIGS. 1-2 and as will be described in greater detail below, anvil (400) is configured to removably couple with shaft assembly (200), adjacent to stapling head assembly (300). As will also be described in greater detail below, anvil (400) and stapling head assembly (300) are configured to cooperate to manipulate tissue in three ways, including clamping the tissue, cutting the tissue, and stapling the tissue. A rotatable knob (130) at the proximal end of handle assembly (100) is rotatable to provide precise clamping of the tissue between anvil (400) and stapling head assembly (300). When a safety trigger (140) of handle assembly (100) is pivoted away from a firing trigger (150) of handle assembly (100), firing trigger (150) may be actuated to thereby provide cutting and stapling of the clamped tissue.

A. Exemplary Anvil

Figure 3:
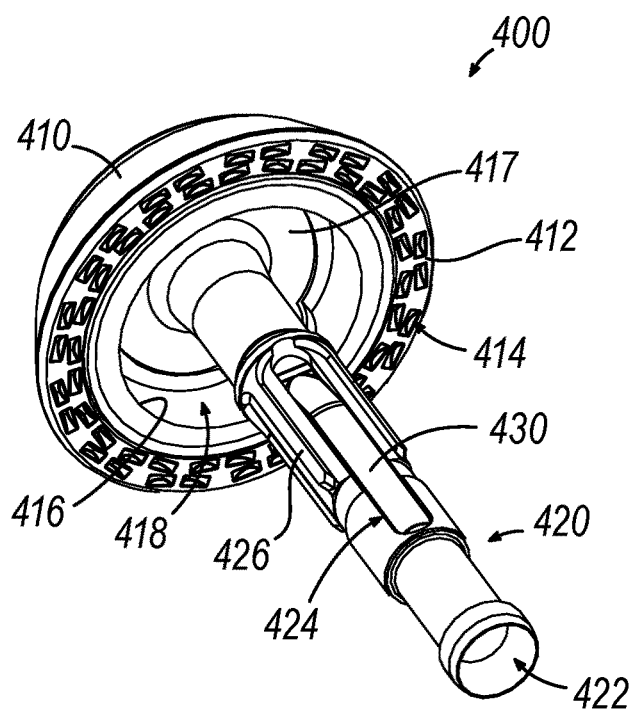
FIG. 3 depicts a perspective view of the anvil of the circular stapler of FIG. 1.

As best seen in FIG. 3, anvil (400) of the present example comprises a head (410) and a shank (420). Head (410) includes a proximal stapling surface (412) that defines a plurality of staple forming pockets (414). Staple forming pockets (414) are arranged in two concentric annular arrays in the present example. Staple forming pockets (414) are configured to deform staples as the staples are driven into staple forming pockets (414). Proximal stapling surface (412) terminates at an inner edge (416), which defines an outer boundary of an annular recess (418) surrounding shank (420). A breakable washer (417) is positioned within annular recess (418) and is configured to provide the operator with a tactile and audible indication that a distal firing stroke has been completed, in addition to serving as a cutting board, as described in greater detail below.

Shank (420) defines a bore (422) and includes a pair of pivoting latch members (430). Latch members (430) are positioned within bore (422) such that distal ends (434) are positioned at the proximal ends of lateral openings (424), which are formed through the sidewall of shank (420). Latch members (430) thus act as retaining clips. This allows anvil (400) to be removably secured to an actuatable closure member in the form of a trocar (330) of stapling head assembly (300), as will be described in greater detail below. Shank (420) of anvil (400) and trocar (330) of stapling head assembly (300) thus cooperate with one another as coupling members.

B. Exemplary Stapling Head Assembly

Figure 4:
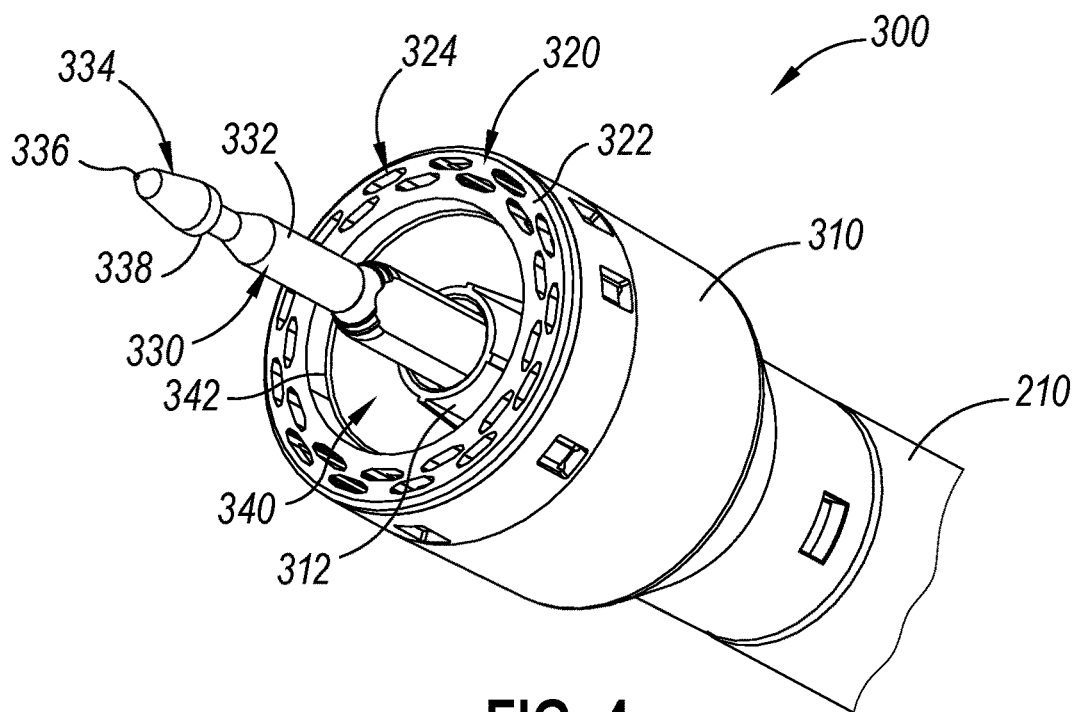
FIG. 4 depicts a perspective view of the stapling head assembly of the circular stapler of FIG. 1.
Figure 5:
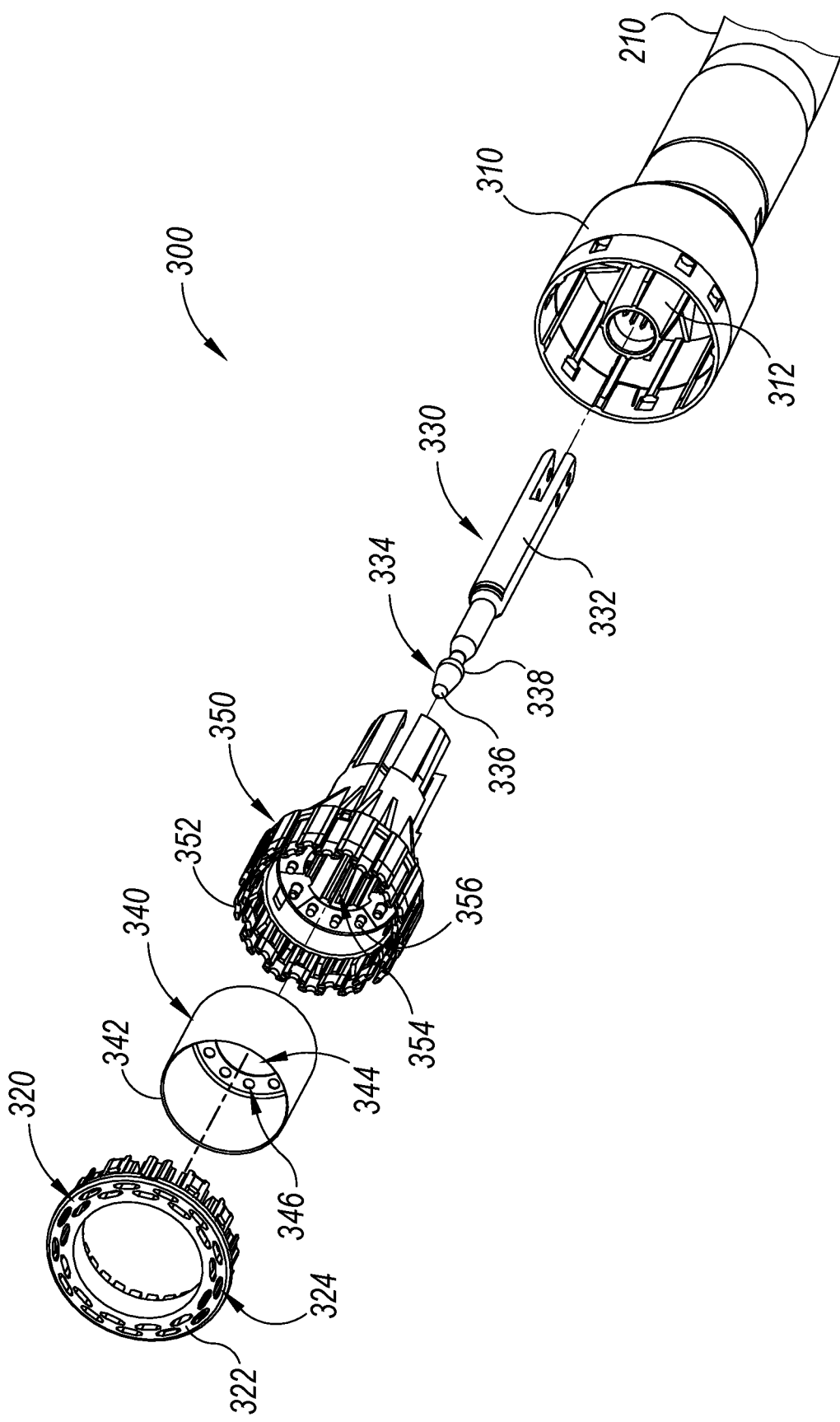
FIG. 5 depicts an exploded perspective view of the stapling head assembly of FIG. 4.

As best seen in FIGS. 4 and 5, stapling head assembly (300) of the present example is coupled to a distal end of shaft assembly (200) and comprises a tubular body member (310) and a staple driver member (350) slidably housed therein. Body member (310) includes a distally extending cylindraceous inner core member (312) positioned coaxially therein. Body member (310) is fixedly secured to an outer sheath (210) of shaft assembly (200), and body member (310) and outer sheath (210) thus serve together as a mechanical ground for stapling head assembly (300).

Trocar (330) is positioned coaxially within inner core member (312) of body member (310). As will be described in greater detail below, trocar (330) is operable to translate distally and proximally relative to body member (310) in response to rotation of knob (130) relative to casing (110) of handle assembly (100). Trocar (330) comprises a shaft (332) and a head (334). Head (334) includes a pointed tip (336) and a radially inwardly extending proximal surface (338). Head (334) and the distal portion of shaft (332) are configured for insertion into bore (422) of anvil (400). Proximal surface (338) and latch shelves (436) have complementary positions and configurations such that latch shelves (436) engage proximal surface (338) when shank (420) of anvil (400) is fully seated on trocar (330). Anvil (400) is thus secured to trocar (330) through a snap fit provided by latch members (430).

Staple driver member (350) is operable to actuate longitudinally within body member (310) in response to activation of motor (160) as will be described in greater detail below. As shown best in FIG. 5, staple driver member (350) of the present example includes two distally presented concentric annular arrays of staple drivers (352). Staple drivers (352) are arranged to correspond with the arrangement of staple forming pockets (414) of anvil (400). Thus, each staple driver (352) is configured to drive a corresponding staple distally into a corresponding staple forming pocket (414) when stapling head assembly (300) is actuated (or "fired"). Staple driver member (350) also defines a bore (354) that is configured to coaxially and slidably receive core member (312) of body member (310). An annular array of studs (356) project distally from a distally presented surface surrounding bore (354).

A cylindraceous knife member (340) is coaxially positioned within a distally-opening central recess of staple driver member (350) that communicates with bore (354). Knife member (340) includes a distally presented, sharp circular cutting edge (342). Knife member (340) is sized such that knife member (340) defines an outer diameter that is just smaller than the diameter defined by the radially inner-most surfaces of the inner annular array of staple drivers (352). Knife member (340) also defines a central opening that is configured to coaxially receive core member (312) of body member (310). An annular array of openings (346) formed in knife member (340) is configured to mate with the annular array of studs (356) of staple driver member (350), such that knife member (340) is fixedly secured to staple driver member (350) via studs (356) and openings (346).

Figure 9:
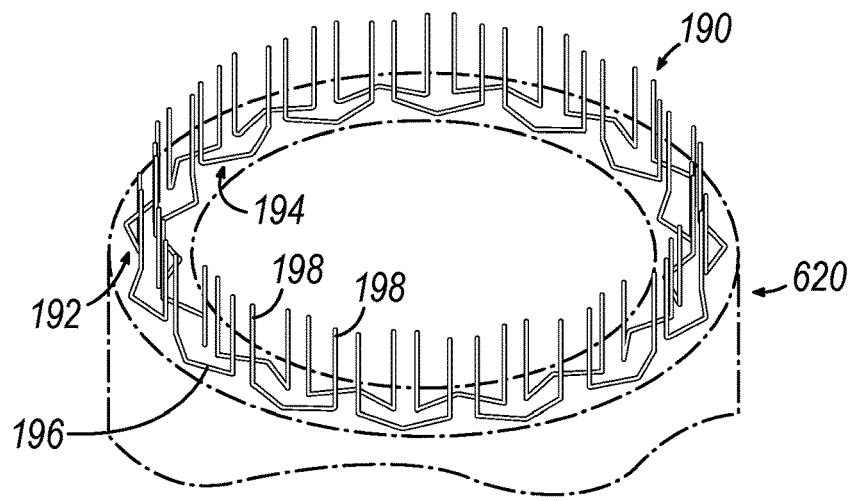
FIG. 9 depicts a perspective view of portions the stapling head assembly of FIG. 8, showing an array of expandable staples in an unformed state.

An annular deck member (320) is fixedly secured to a distal end of body member (310). Deck member (320) includes a distally presented stapling surface in the form of a deck surface (322) having two concentric annular arrays of staple openings (324). Staple openings (324) are arranged to align with the arrangement of staple drivers (352) of staple driver member (350) and staple forming pockets (414) of anvil (400) described above. Each staple opening (324) is configured to slidably receive and provide a pathway for a corresponding staple driver (352) to drive a corresponding staple distally through deck member (320) and into a corresponding staple forming pocket (414) when stapling head assembly (300) is actuated. As best seen in FIG. 9, deck member (320) has a central opening that defines an inner diameter that is just slightly larger than the outer diameter defined by knife member (340). Deck member (320) is thus configured to permit knife member (340) to translate longitudinally through the central opening concurrently with longitudinal translation of staple driver member (350). In particular, knife member (340) is configured to actuate relative to deck member (340) between a proximal retracted position and a distal extended position, where cutting edge (342) is proximal to deck surface (322) in the proximal retracted position and distal to deck surface (322) in the distal extended position.

C. Exemplary Shaft Assembly

Figure 6:
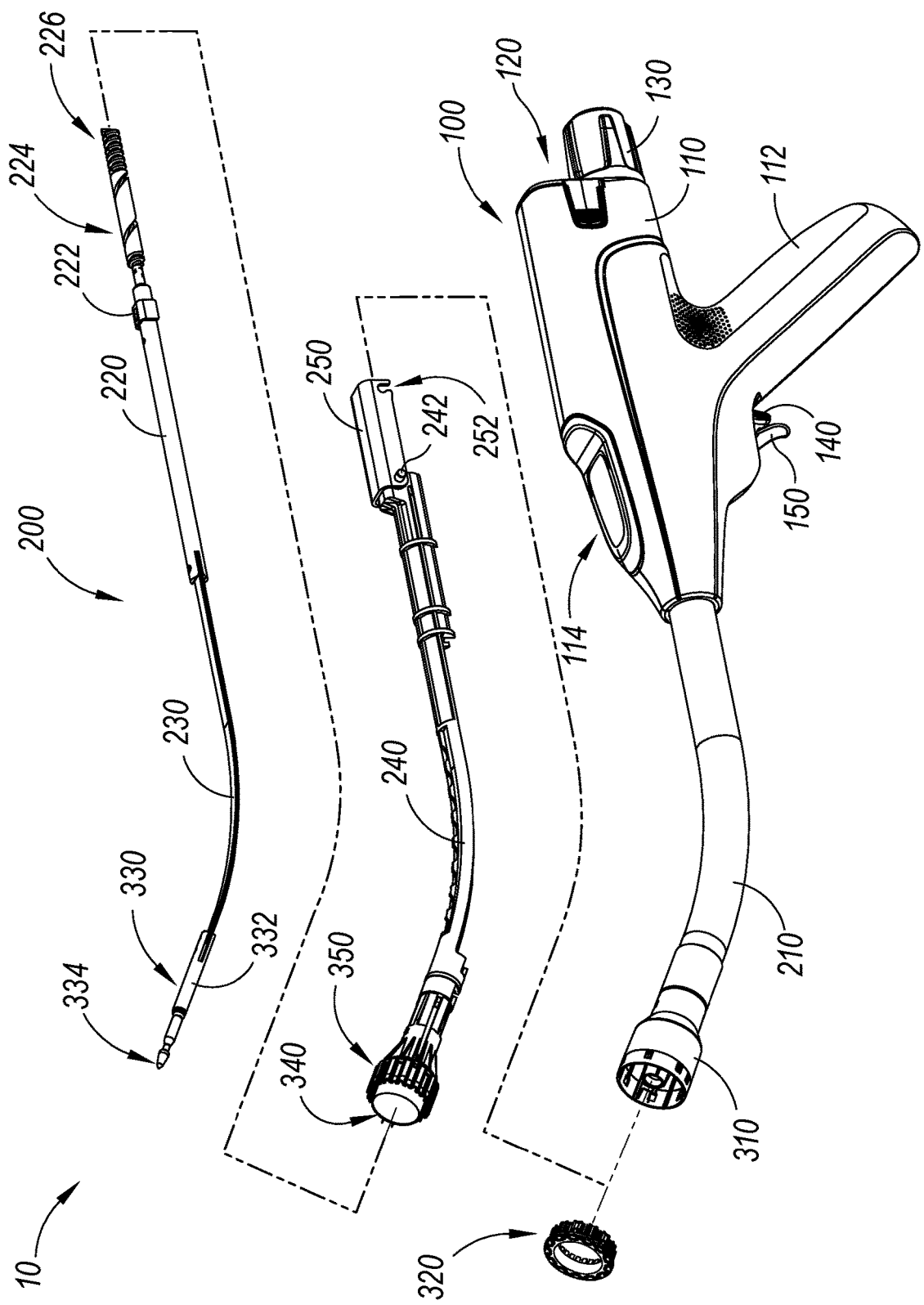
FIG. 6 depicts an exploded perspective view of the circular stapler of FIG. 1, with portions of the shaft assembly shown separated from each other.

FIG. 6 shows various components of shaft assembly (200), which operatively couple components of stapling head assembly (300) with components of handle assembly (100). In particular, and as noted above, shaft assembly (200) includes an outer sheath (210) that extends between handle assembly (100) and body member (310) and includes a medial portion that extends along a curved path.

Shaft assembly (200) further includes a trocar actuation rod (220) having a proximal end operatively coupled with rotatable knob (130) and a distal end coupled with a flexible trocar actuation band assembly (230), the assembly of which is slidably housed within outer sheath (210). The distal end of trocar actuation band assembly (230) is fixedly secured to the proximal end of trocar shaft (332), such that trocar (330) will translate longitudinally relative to outer sheath (210) in response to translation of trocar actuation band assembly (230) and trocar actuation rod (220) relative to outer sheath (210), which occurs in response to rotation of rotatable knob (130). A clip (222) is fixedly secured to trocar actuation rod (220) and is configured to cooperate with complementary features within handle assembly (100) to prevent trocar actuation rod (220) from rotating within handle assembly (100) while still permitting trocar actuation rod (220) to translate longitudinally within handle assembly (100). Trocar actuation rod (220) further includes a section of coarse helical threading (224) and a section of fine helical threading (226) proximal to coarse helical threading (224), which are configured to control a rate of longitudinal advancement of trocar actuation rod (220), as described in greater detail below.

Shaft assembly (200) further includes a stapling head assembly driver (240) that is slidably housed within outer sheath (210) and about the combination of trocar actuation rod (220) and trocar actuation band assembly (230). Stapling head assembly driver (240) includes a distal end that is fixedly secured to the proximal end of staple driver member (350), a proximal end secured to a drive bracket (250) via a pin (242), and a flexible section disposed therebetween. It should therefore be understood that staple driver member (350) will translate longitudinally relative to outer sheath (210) in response to translation of stapling head assembly driver (240) and drive bracket (250) relative to outer sheath (210).

D. Exemplary Handle Assembly and User Input Features

As shown in FIG. 1, handle assembly (100) includes a casing (110) having a lower portion that defines an obliquely oriented pistol grip (112) and an upper portion that supports a user interface feature (114) and releasably receives a battery pack (120), as described in greater detail below. Handle assembly (100) further includes several features that are operable to actuate anvil (400) and stapling head assembly (300). In particular, handle assembly (100) includes a rotatable knob (130), a safety trigger (140), a firing trigger (150), a motor (160), and a motor activation module (180). Knob (130) is coupled with trocar actuation rod (220) via a nut (not shown), such that coarse helical threading (224) will selectively engage a thread engagement feature within the interior of the nut; and such that fine helical threading (226) will selectively engage a thread engagement feature within the interior of knob (130). These complementary structures are configured such that trocar actuation rod (220) will first translate proximally at a relatively slow rate, and then translate proximally at a relatively fast rate, in response to rotation of knob (130).

It should be understood that when anvil (400) is coupled with trocar (330), rotation of knob (130) will provide corresponding translation of anvil (400) relative to stapling head assembly (300). It should also be understood that knob (130) may be rotated in a first angular direction (e.g., clockwise) to retract anvil (400) proximally toward stapling head assembly (300); and in a second angular direction (e.g., counterclockwise) to extend anvil (400) distally away from stapling head assembly (300). Knob (130) may thus be used to adjust a gap distance (d) between opposing stapling surfaces (412, 322) of anvil (400) and stapling head assembly (300) until a suitable gap distance (d) has been achieved, for example as shown in FIG. 7C described below.

Firing trigger (150) is operable to activate motor (160) to thereby actuate stapling head assembly (300) to staple and cut tissue clamped between anvil (400) and stapling head assembly (300). Safety trigger (140) is operable to selectively block actuation of firing trigger (150) based on the longitudinal position of anvil (400) in relation to stapling head assembly (300). Handle assembly (100) also includes components that are operable to selectively lock out both triggers (140, 150) based on the position of anvil (400) relative to stapling head assembly (300). For instance, safety trigger (140) may be blocked from rotating from an engaged position to a disengaged position until the position of anvil (400) relative to stapling head assembly (300) is within a predefined range. Accordingly, until the anvil position is within the predefined range, actuation of firing trigger (150) is blocked by safety trigger (140), thereby inhibiting firing of stapling head assembly (300).

Firing trigger (150) is operable to actuate a switch of motor activation module (180) (FIG. 1) when firing trigger (150) is pivoted proximally to a fired position. Motor activation module (180) is in communication with battery pack (120) and motor (160), such that motor activation module (180) is configured to provide activation of motor (160) with electrical power from battery pack (120) in response to firing trigger (150) actuating the switch of motor activation module (180). Thus, motor (160) will be activated when firing trigger (150) is pivoted. This activation of motor (160) will actuate stapling head assembly (300) via drive bracket (250), as described in greater detail below.

E. Exemplary Anastomosis Procedure with Circular Stapling Instrument

FIGS. 7A-7E show instrument (10) being used to form an anastomosis (70) between two tubular anatomical structures (20, 40). By way of example only, the tubular anatomical structures (20, 40) may comprise sections of a patient's esophagus, colon, or other portions of the patient's digestive tract, or any other tubular anatomical structures.

Figure 7A:
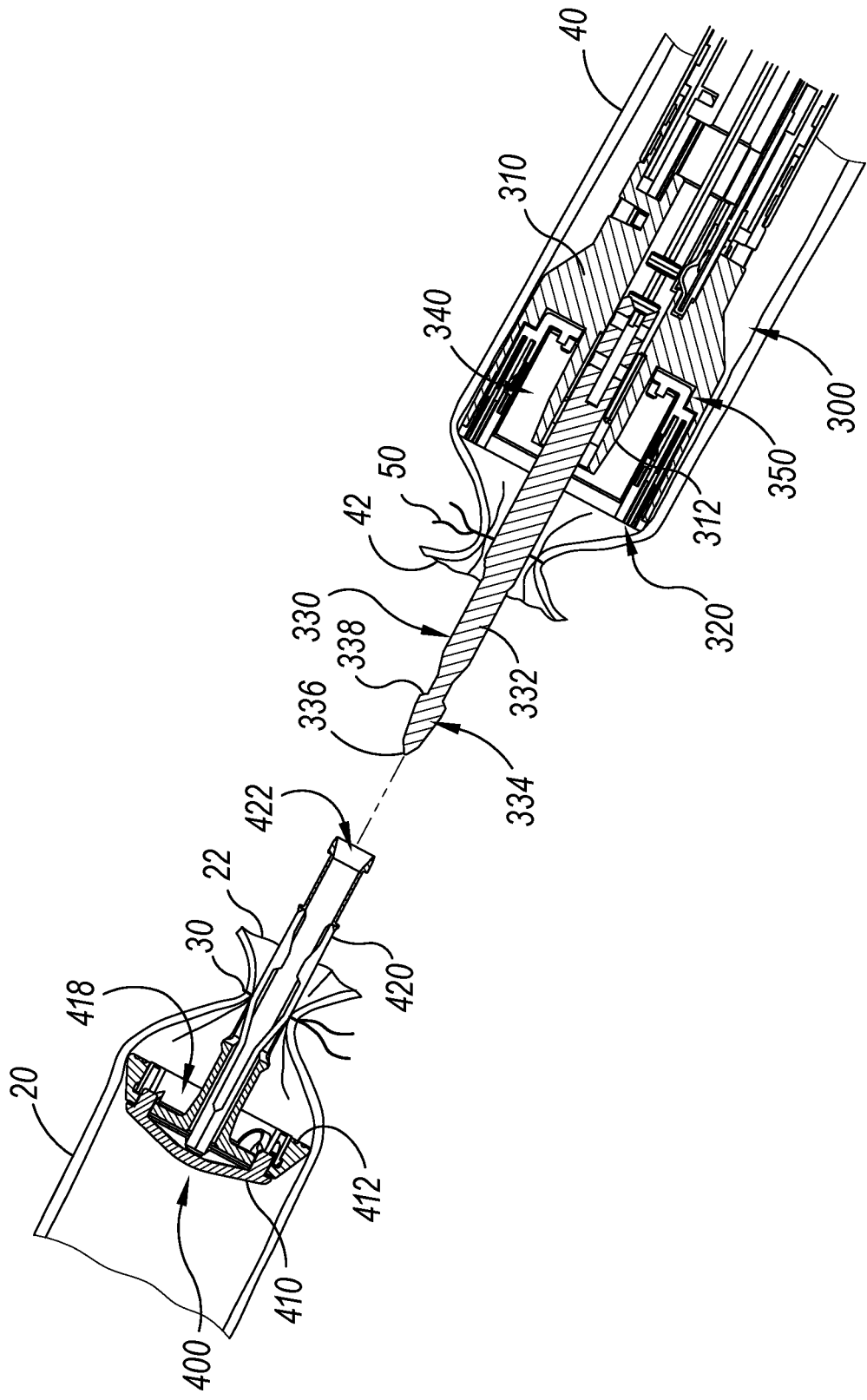
FIG. 7A depicts a cross-sectional side view of the anvil of FIG. 3 positioned within a first section of a digestive tract and the stapling head assembly of FIG. 4 positioned within a separate second section of the digestive tract, with the anvil separated from the stapling head assembly.

As shown in FIG. 7A, anvil (400) is positioned in one tubular anatomical structure (20) and stapling head assembly (300) is positioned in another tubular anatomical structure (40). As shown in FIG. 7A, anvil (400) is positioned in tubular anatomical structure (20) such that shank (420) protrudes from the open severed end (22) of tubular anatomical structure (20). In the present example, purse-string suture (30) is provided about a mid-region of shank (420) to generally secure the position of anvil (400) in tubular anatomical structure (20). Stapling head assembly (300) is positioned in tubular anatomical structure (40) such that trocar (330) protrudes from the open severed end (42) of tubular anatomical structure (20). A purse-string suture (50) is provided about a mid-region of shaft (332) to generally secure the position of stapling head assembly (300) in tubular anatomical structure (40). Stapling head assembly (300) is then urged distally to ensure that stapling head assembly (300) is fully seated at the distal end of tubular anatomical structure (40).

Figure 7B:
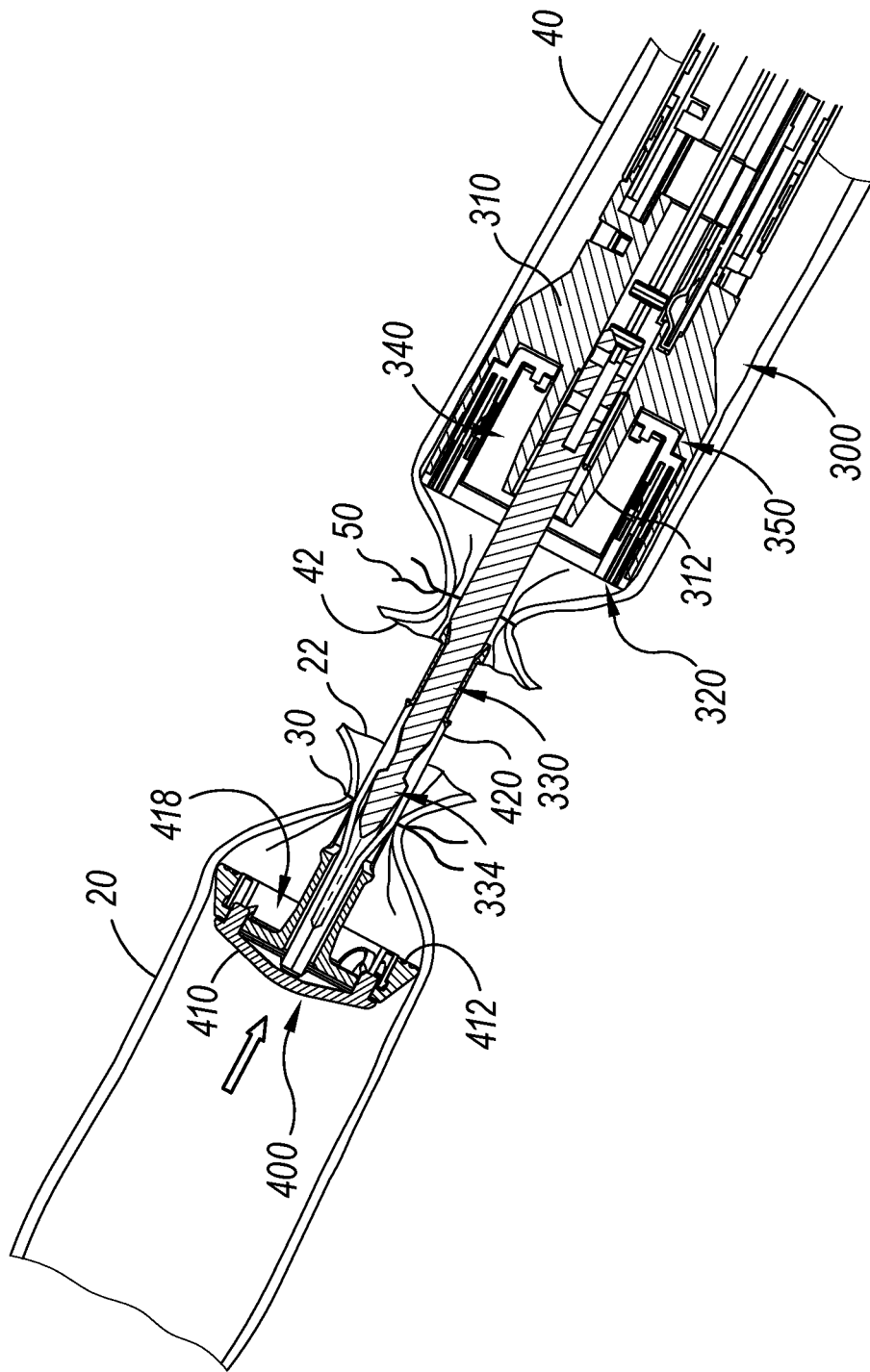
FIG. 7B depicts a cross-sectional side view of the anvil of FIG. 3 positioned within the first section of the digestive tract and the stapling head assembly of FIG. 4 positioned within the separate second section of the digestive tract, with the anvil secured to the stapling head assembly.
Figure 7C:
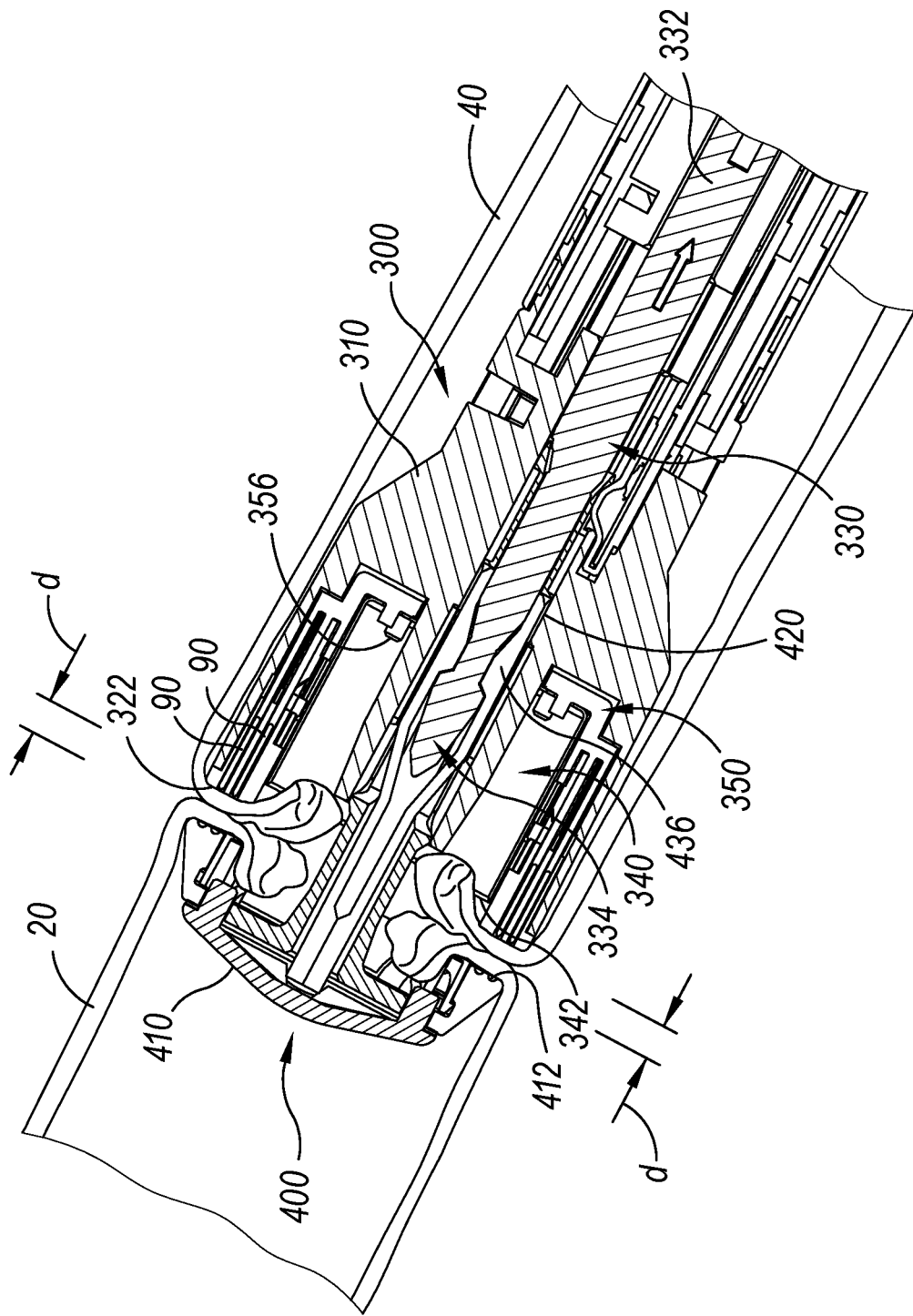
FIG. 7C depicts a cross-sectional side view of the anvil of FIG. 3 positioned within the first section of the digestive tract and the stapling head assembly of FIG. 4 positioned within the separate second section of the digestive tract, with the anvil retracted toward the stapling head assembly to thereby clamp tissue between the anvil and the stapling head assembly.

Next, anvil (400) is secured to trocar (330) by inserting trocar (330) into bore (422) as shown in FIG. 7B. Latch members (430) of anvil (400) engage head (334) of trocar (330), thereby providing a secure fit between anvil (400) and trocar (330). The operator then rotates knob (130) while holding casing (110) stationary via pistol grip (112). This rotation of knob (130) causes trocar (330) and anvil (400) to retract proximally. As shown in FIG. 7C, this proximal retraction of trocar (330) and anvil (400) compresses the tissue of tubular anatomical structures (20, 40) between surfaces (412, 322) of anvil (400) and stapling head assembly (300). As this occurs, the operator may observe the tactile resistance or feedback via knob (130) while turning knob (130), with such tactile resistance or feedback indicating that the tissue is being compressed. As the tissue is being compressed, the operator may visually observe the position of an indicator needle (not shown) within user interface feature (114) of handle assembly (100) to determine whether the gap distance (d) between opposing surfaces (412, 322) of anvil (400) and stapling head assembly (300) is appropriate; and make any necessary adjustments via knob (130).

Once the operator has appropriately set the gap distance (d) via knob (130), the operator pivots safety trigger (140) toward pistol grip (112) to enable actuation of firing trigger (150). The operator then pivots firing trigger (150) toward pistol grip (112), thus causing firing trigger (150) to actuate the switch of motor activation module (180) and thereby activate motor (160) to rotate. This rotation of motor (160) causes actuation (or "firing") of stapling head assembly (300) by actuating drive bracket (250) distally to thereby drive knife member (340) and staple driver member (350) distally together, as shown in FIG. 7D.

As knife member (340) translates distally, cutting edge (342) of knife member (340) cuts excess tissue that is positioned within annular recess (418) of anvil (400) and the interior of knife member (340). Additionally, washer (417) positioned within annular recess (418) of anvil (400) is broken by knife member (340) when the knife member (340) completes a full distal range of motion from the position shown in FIG. 7C to the position shown in FIG. 7D. It should be understood that washer (417) may also serve as a cutting board for knife member (340) to assist in cutting of tissue.

Figure 7D:
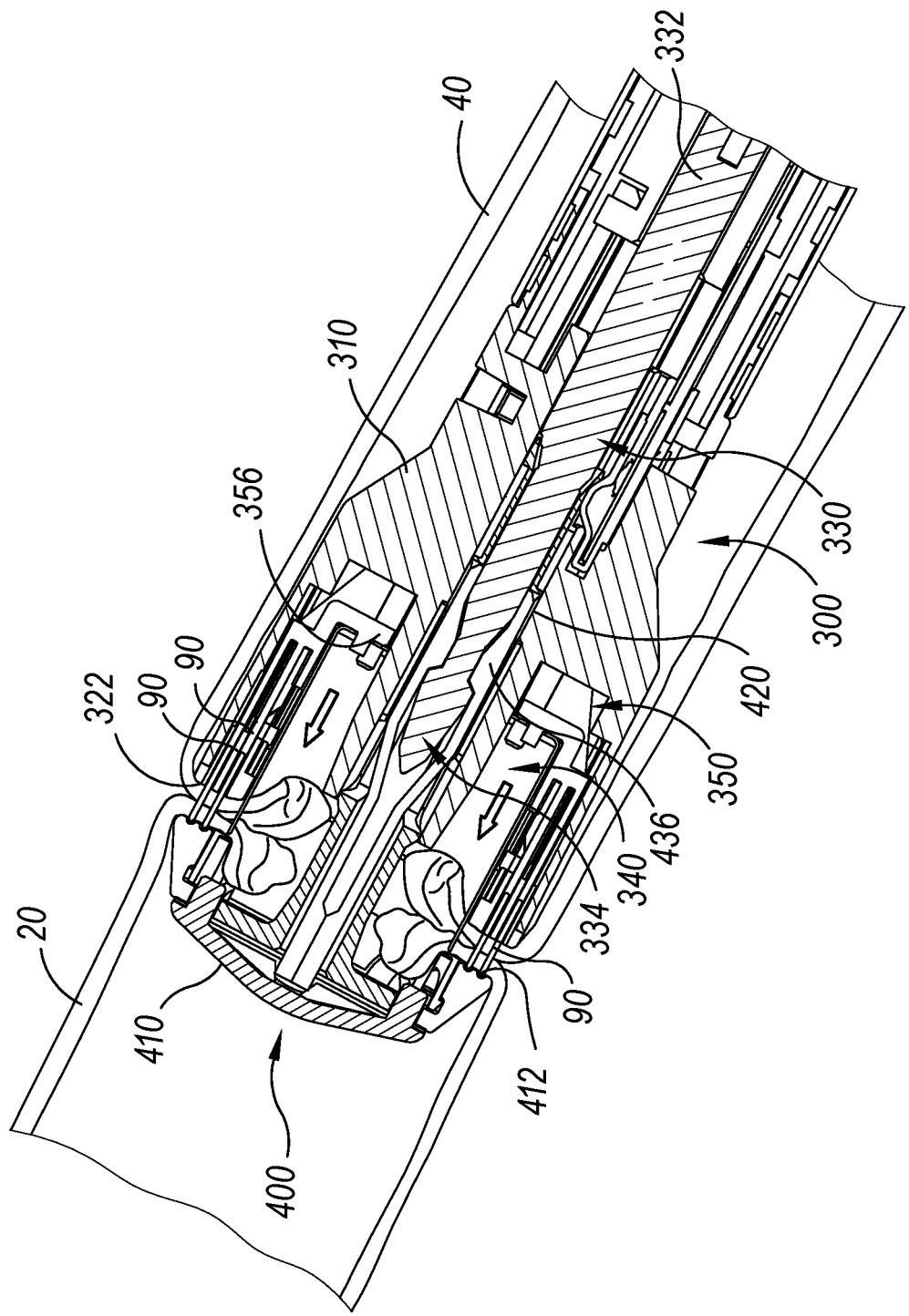
FIG. 7D depicts a cross-sectional side view of the anvil of FIG. 3 positioned within the first section of the digestive tract and the stapling head assembly of FIG. 4 positioned within the second section of the digestive tract, with the stapling head assembly actuated to sever and staple the clamped tissue and thereby joining the first and second sections of the digestive tract.

As staple driver member (350) translates distally from the position shown in FIG. 7C to the position shown in FIG. 7D, staple driver member (350) drives staples (90) through the tissue of tubular anatomical structures (20, 40) and into staple forming pockets (414) of anvil (400). Staple forming pockets (414) deform the driven staples (90) into a "B" shape or a three-dimensional shape, for example, such that the formed staples (90) secure the ends of tissue together, thereby coupling tubular anatomical structure (20) with tubular anatomical structure (40).

Figure 7E:
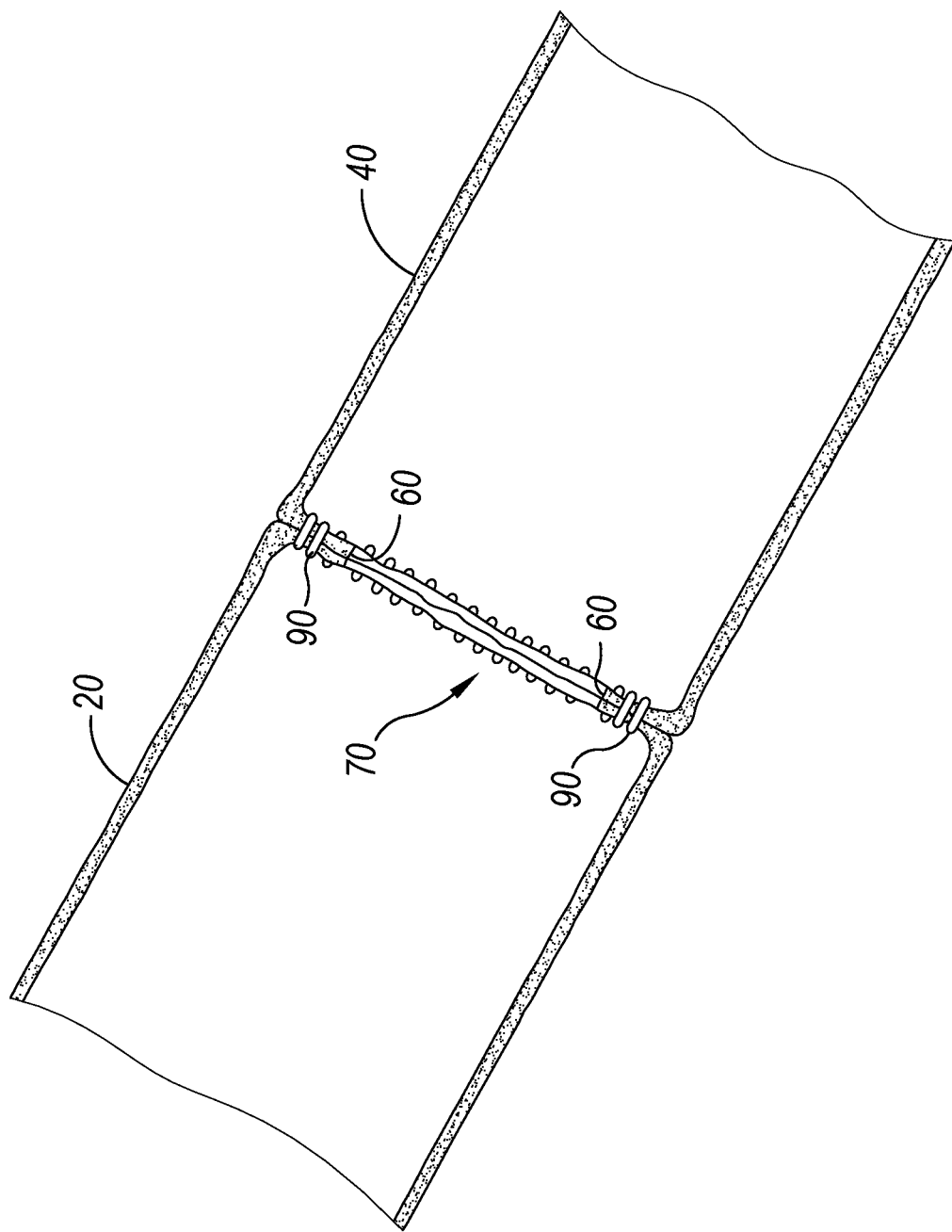
FIG. 7E depicts a cross-sectional side view of the first and second sections of the digestive tract of FIG. 7A joined together at an end-to-end anastomosis formed with the circular stapler of FIG. 1.

After the operator has actuated (or "fired") stapling head assembly (300) as shown in FIG. 7D, the operator rotates knob (130) to drive anvil (400) distally away from stapling head assembly (300), thereby increasing the gap distance (d) to facilitate release of the tissue between surfaces (412, 322). The operator then removes instrument (10) from the patient, with anvil (400) still secured to trocar (330). With instrument (10) removed, the tubular anatomical structures (20, 40) are left secured together by two annular arrays of staples (90) at an anastomosis (70) as shown in FIG. 7E. The inner diameter of the anastomosis (70) is defined by the severed edge (60) left by knife member (340).

II. Exemplary Stapling Head Assembly with Staples Having Expandable Crowns

As noted above, the inner diameter of anastomosis (70) formed by instrument (10) is defined by the outer diameter of knife member (340). Because knife member (340) is smaller than the inner diameters of tubular anatomical structures (20, 40), the resulting diameter of anastomosis (70) is generally smaller than that of each tubular anatomical structure (20, 40). Additionally, the configuration of formed staples (90) may inhibit the ability of anastomosis (70) to expand radially.

In some procedures, it may be desirable to form an anastomosis (70) of enlarged diameter and/or to enable the annular arrays of formed staples (90) to expand radially, thereby minimizing strictures, enabling better peristalsis, and minimizing local tension in and resulting damage to the joined portions of tubular anatomical structures (20, 40). Accordingly, in some such instances, it may be desirable to configure stapling head assembly (300) and anvil (400) with features that enable formation of such an anastomosis and/or patterns of formed staples (90). Exemplary versions of such features are described in greater detail below.

A. Exemplary Stapling Head Assembly with "V" Shaped Expandable Staples

FIGS. 8-12 illustrate portions of an exemplary stapling head assembly (600) that is similar to exemplary stapling head assembly (300) described above. In some versions, stapling instrument (10) can be fitted with stapling head assembly (600) instead of stapling head assembly (300) and be operable as described above. Stapling head assembly (600) is configured the same as stapling head assembly (300) except stapling head assembly (600) includes deck member (620) with deck surface (622) and staple openings (624). Also, staple driver member (350), when used with stapling head assembly (600) is configured with staple drivers (652) that have a differing shape from staple drivers (352) as will be discussed further below. Furthermore, stapling head assembly (600) is configured for use with expandable staples generally having a "V" shape as will be described further below.

1. Exemplary Expandable Staples with "V" Shaped Crown

Figure 8:
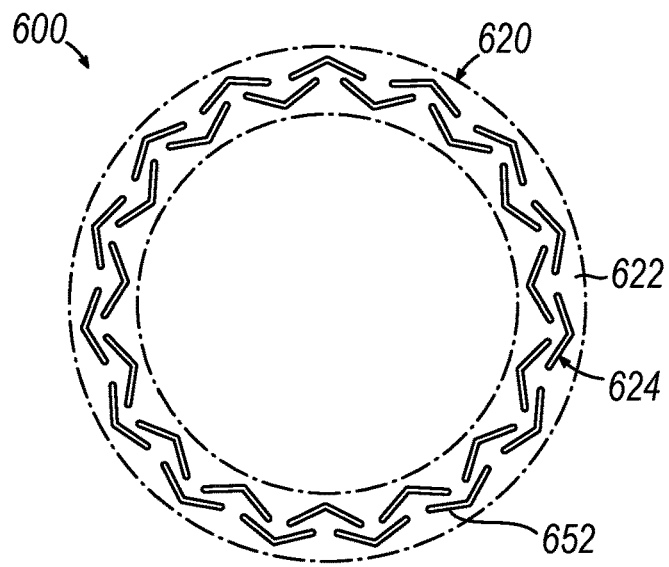
FIG. 8 depicts a top view of portions of an exemplary alternate stapling head assembly for use with the instrument of FIG. 1.

Referring to FIGS. 8-12, stapling head assembly (600) is configured for use with expandable staples (190). In the present example, staples (190) are configured with a "V" shape that allows each staple (190) to expand after being deployed as will be discussed in greater detail below. Referring to FIG. 8, deck member (620) is shown with deck surface (622) having "V" shaped openings (624). With staples (190) not shown in FIG. 8, staples drivers (652) are visible through openings (624). As shown, staple drivers (652) have a corresponding "V" shape to openings (624) such that staple drivers (652) are configured to deploy staples (190), with their "V" shape, through openings (624).

Referring to FIG. 9, a portion of deck member (620) is shown in phantom to reveal a plurality of undeployed staples (190) loaded within deck member (620). As shown in the present example, staples (190) are arranged in two annular or ring-shaped rows where there is an outer row (192) and an inner row (194). Staples (190) are further arranged such that each row is staggered or offset from the other, and such that staples (190) in one row oppose staples (190) in the other row. With this opposing arrangement, staples (190) in one row are effectively rotated 180 degrees from staples (190) in the other row. In some versions, the size and/or shape of staples (190) in inner row (194) can differ from that of outer row (192) to assist in establishing the circular staple pattern shown.

Figure 10:
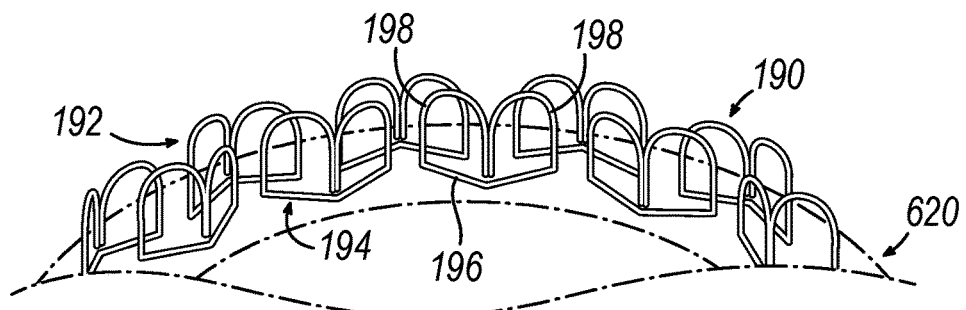
FIG. 10 depicts a partial perspective view of the staples of FIG. 9, shown in a formed state.

Staples (190) each comprise a crown (196) and a pair of legs (198). Furthermore, staples (190) have a "V" shape where a top view looking down onto crown (196) presents a "V" shape. The "V" shape can further be described as having two straight portions or lines with a vertex between them. In this fashion, staples (190) define an angle between the pair of legs (198). As understood from comparing FIGS. 9 and 10, staples (190) have this "V" shape in both the undeployed state as shown in FIG. 9 and in the deployed state as shown in FIG. 10. As shown in FIG. 10, when staples (190) are deployed or fired from instrument (10), as described above, the interaction of staples (190) with anvil (400) deforms the pair of legs (198) to bend them in a curved manner forming a "B" shape.

Figure 11:
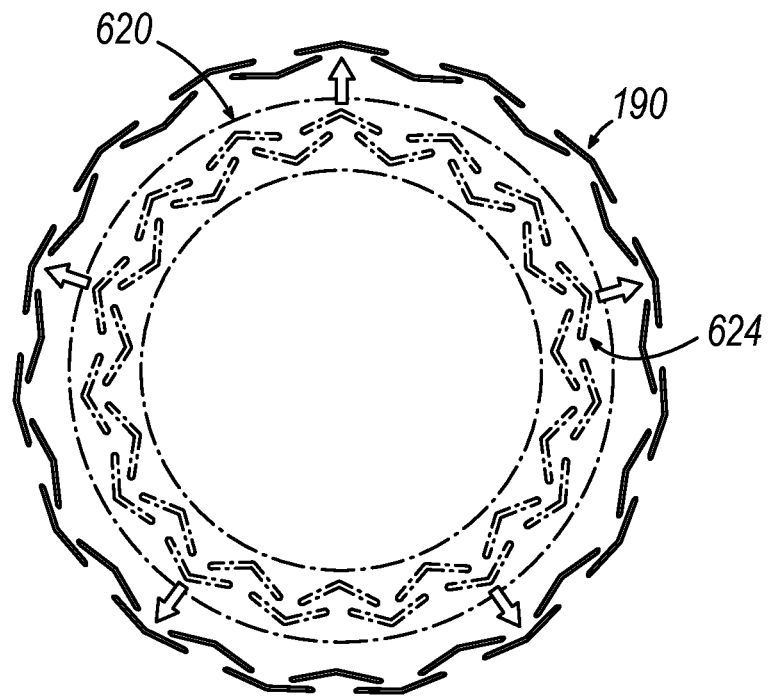
FIG. 11 depicts a top view of portions of the stapling head assembly of FIG. 8, showing the movement of the staple line based on staple expansion.
Figure 12:
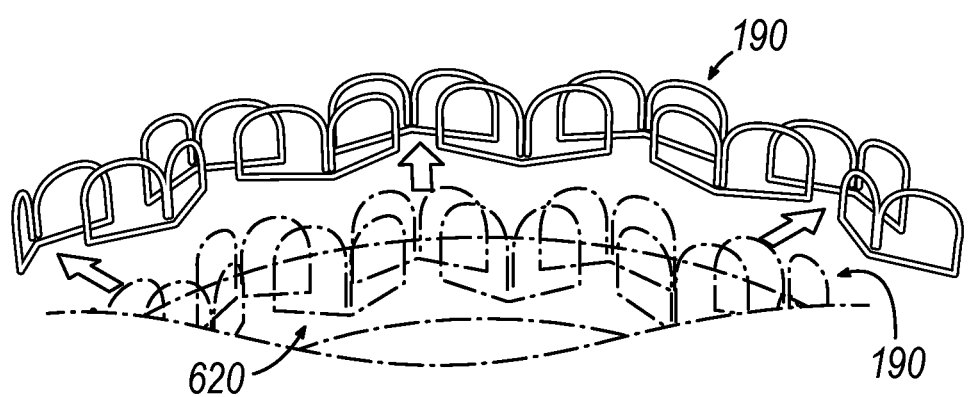
FIG. 12 depicts a partial perspective view of the formed staples of FIG. 10, showing the movement of the staple line based on staple expansion.

Referring now to FIGS. 11 and 12, staples (190) are configured as expandable staples. For instance, FIG. 11 illustrates the staple deck (620) showing openings (624) from which staples (190) would have initially been deployed. As shown in FIG. 11 and further in FIG. 12, after staples (190) have been deployed they may undergo an expansion allowing them to move radially. This expansion allows for the plurality of staples (190) forming the ring shape or pattern to define a first or initial diameter, and then subsequently allowing the same plurality of staples (190) to define a second or subsequent diameter that is larger than the initial diameter. In this manner, the diameter of the lumen at the anastomosis is increased.

In the present example, the "V" shape configuration of staples (190) contributes to the ability of staples (190) to expand or be expandable. In some versions, staples (190) are formed with the "V" shape and after deployment, staples (190) can experience tension based on radial tissue forces, e.g., from peristalsis, or from the passage of material through the lumen. In response to experiencing this tension, legs (198) of staples (190) deflect from the vertex to define a larger angle between the pair of legs (198). Consequently, the width of staples (190) increase, with the width being defined as the linear distance between the pair of legs (198).

In other versions, staples (190) initially have a straight or substantially straight shape and are bent when loaded within instrument (10). For instance, staples (190) may be bent into a "V" shape when loaded within annular deck member (320). In this manner, staples (190) are under tension when deployed, but then after deployment, staples (190) return to their relaxed state and thus expand radially by expanding to a straighter shape. In this version, staples (190) automatically expand after being deployed without needing any tissue force placed upon staples (190) to achieve expansion of staples (190). As will be described further below, other "V" shape staples having other features that promote expandability can be used with instrument (10) and stapling head assembly (600) in place of staples (190).

2. Exemplary Expandable Staples with "V" Shaped Crown and Spring Feature

FIG. 13 depicts an exemplary staple (290), which can replace staple (190) or (90) in the plurality of staples. Staple (290) includes crown (296) and a pair of legs (298). Crown (296) includes two straight portions (297) and a spring feature (295). Spring feature (295) in the present example is located between each of straight portions (297) and is formed with a curved shape. In the unexpanded state as shown in FIG. 13, staple (290) defines an angle (α) between straight portions (297), and staple (290) defines a distance (d) between legs (298). After deployment and after staple (290) expands the same or similar to the expansion described above with respect to staple (190), staple (290) expands about spring feature (295) such that angle (α) increases, which also corresponds with an increase in distance (d). This produces a broader "V" shape for staples (290) that resembles staples (290) becoming closer to linear shaped.

In the present example, staple (290) starts initially as straight or substantially straight and adopts its "V" shape with incorporated spring feature (295) during loading with instrument (10) such that staples (290) are held within instrument (10) under tension. Moreover, staples (290) are formed of fully or partially resilient material such that after being deployed, spring feature (295) assists in automatically expanding staples (290) as they return to their relaxed state. During this expansion, staples (290) increase in width (d) between legs (298), which widens the diameter of the anastomosis.

In some other versions, staple (290) is formed such that in its relaxed state staple (290) has the "V" shape with spring feature (295). In these versions, spring feature (295) promotes expansion of staple (290) based on tissue forces described above acting on staple (290). For instance, spring feature (295) is coplanar with crown (296) and legs (298) extend generally orthogonal to a plane defined by crown (296) and spring feature (295). After deployment of staple (290), tension from radial tissue forces act on staple (290) and such forces are generally orthogonal to axes defined by legs (298) when legs (298) are in the unformed state. In this manner, spring feature (295) is configured and oriented so that when radial tissue forces act on staple (290), expansion of staple (290) occurs as described above. In view of the teachings herein, other ways to configure staple (290) with spring feature (295) will be apparent to those of ordinary skill in the art.

3. Exemplary Expandable Staples with "V" Shaped Crown and Weakened Region

FIGS. 14A and 14B illustrate another exemplary staple (390) which can replace staple (190) or (90) in the plurality of staples. Staple (390) includes crown (396) and a pair of legs (398). Crown (396) includes two straight portions (397) and a weakened region (395). Weakened region (395) in the present example is located between each of straight portions (397) and is formed as a notch or cut-away portion of crown (396). This configuration for weakened region (395) provides for a thinner portion of crown (396) at the junction or vertex of straight portions (397) where there is less material present. This in turn allows for staple (390) to be more responsive to expand when lower tissue forces act on staple (390).

In the undeployed state as shown in FIG. 14A, staple (390) defines an angle ($\alpha 1$) between straight portions (397), and staple (390) defines a distance (d1) between legs (398). After deployment as shown in FIG. 14B, and after staple (390) is subject to tension from tissue forces as described above, staple (390) expands about weakened region (395) such that angle ($\alpha 1$) increases, which also corresponds with an increase in distance (d1). This produces a broader "V" shape for staples (390) that resembles staples (390) becoming closer to linear shaped. In the present example, staple (390) with weakened region (395) is configured such that it plastically deforms when the tissue forces act on staple (390) as described above. In this manner, the increased diameter at the anastomosis can be maintained.

As shown in FIGS. 14A and 14B, weakened region (395) is coplanar with crown (396). Additionally, legs (398) extend generally orthogonal to a plane defined by crown (396) and weakened region (395). After deployment of staples (390), tension from radial tissue forces act on staple (390) and such forces are generally orthogonal to axes defined by legs (398) when in the unformed state. In this manner, weakened region (395) is configured and oriented so that when radial tissue forces act on staple (390), expansion of staple (390) occurs as described above. In view of the teachings herein, other ways to configure staple (390) with weakened region (395) will be apparent to those of ordinary skill in the art.

FIG. 15 illustrates another exemplary staple (490) which can replace staple (190) or (90) in the plurality of staples. Staple (490) includes crown (496) and a pair of legs (498). Crown (496) includes two straight portions (497) and a weakened region (495). Weakened region (495) in the present example is located between each of straight portions (497) and is formed as a reduced diameter section of crown (496). This configuration for weakened region (495) provides for a smaller portion of crown (496) at the junction or vertex of straight portions (497) where there is less material present. This in turn allows for staple (490) to be more responsive to expand when lower tissue forces act on staple (490).

In the undeployed state as shown in FIG. 15, staple (490) defines an angle (α2) between straight portions (497), and staple (490) defines a distance (d2) between legs (498). After deployment, and after staple (490) is subject to tension from tissue forces as described above, staple (490) expands about weakened region (495) such that angle (α2) increases, which also corresponds with an increase in distance (d2). This produces a broader "V" shape for staples (490) that resembles staples (490) becoming closer to linear shaped. In the present example, staple (490) with weakened region (495) is configured such that it plastically deforms when the tissue forces act on staple (490) as described above. In this manner, the increased diameter at the anastomosis can be maintained.

As shown in FIG. 15, weakened region (495) is coplanar with crown (496). Additionally, legs (498) extend generally orthogonal to a plane defined by crown (496) and spring feature (495). After deployment of staples (490), tension from radial tissue forces act on staple (490) and such forces are generally orthogonal to axes defined by legs (497) when in the unformed state. In this manner, weakened region (495) is configured and oriented so that when radial tissue forces act on staple (490), expansion of staple (490) occurs as described above. In view of the teachings herein, other ways to configure staple (490) with weakened region (495) will be apparent to those of ordinary skill in the art.

Figure 16:
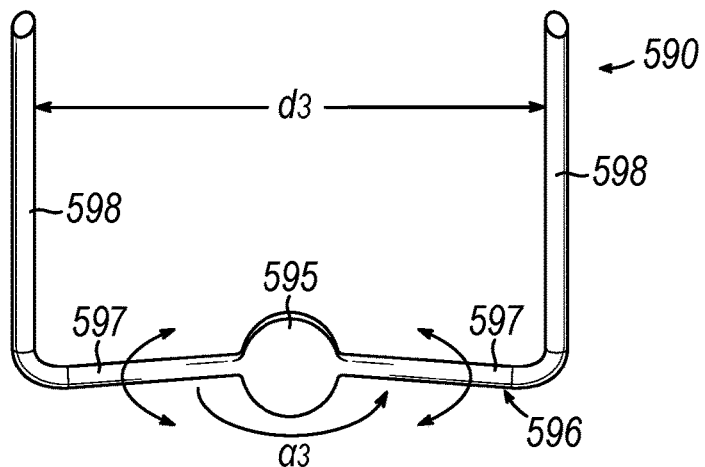
FIG. 16 depicts a front view of an exemplary "V" shaped staple having a flat area feature.

FIG. 16 illustrates another exemplary staple (590) which can replace staple (190) or (90) in the plurality of staples. Staple (590) includes crown (596) and a pair of legs (598). Crown (596) includes two straight portions (597) and a weakened region (595). Weakened region (595) in the present example is located between each of straight portions (597) and is formed as a flat area or portion of crown (596). This configuration for weakened region (595) provides for a more pliable portion of crown (596) at the junction or vertex of straight portions (597) where there is thinner material present. This in turn allows for staple (590) to be more responsive to expand when lower tissue forces act on staple (590).

In the undeployed state as shown in FIG. 16, staple (590) defines an angle (α3) between straight portions (597), and staple (590) defines a distance (d3) between legs (598). After deployment, and after staple (590) is subject to tension from tissue forces as described above, staple (590) expands about weakened region (595) such that angle (α3) increases, which also corresponds with an increase in distance (d3). This produces a broader "V" shape for staples (590) that resembles staples (590) becoming closer to linear shaped. In the present example, staple (590) with weakened region (595) is configured such that it plastically deforms when the tissue forces act on staple (590) as described above. In this manner, the increased diameter at the anastomosis can be maintained.

As shown in FIG. 16, legs (598) extend generally orthogonal to a plane defined by crown (596). Similarly, weakened region (595), and its flat area, extend generally orthogonal to the plane defined by crown (596). In use after deployment of staples (590), tension from radial tissue forces act on staple (590) and such forces are generally orthogonal to axes defined by legs (598) when in the unformed state. Accordingly, in this manner, weakened region (595) is configured and oriented so that when radial tissue forces act on staple (590), expansion of staple (590) occurs as described above. In view of the teachings herein, other ways to configure staple (590) with spring feature (595) will be apparent to those of ordinary skill in the art.

Staples (390, 490, 590) above are described as being pre-formed with a "V" shape and a weakened region (395, 495, 595) where these staples maintain their "V" shape in a relaxed state and expand when subjected to tissue forces. However, in some other versions, staples (390, 490, 590) can be configured similar to staple (290), where staples (390, 490, 590) are initially straight or substantially straight and when loaded within instrument (10), staples (390, 490, 590) are bent to the "V" shape and held under tension. After deployment, staples (390, 490, 590) automatically expand to their relaxed straighter configuration.

4. Exemplary Expandable Staples with "V" Shaped Crown and Hinge Feature

Figure 17:
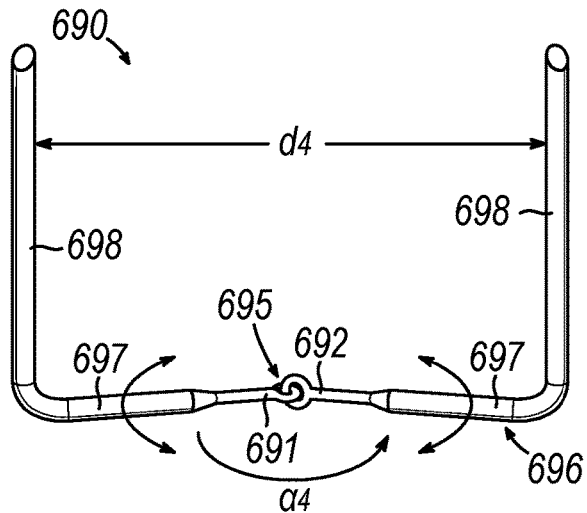
FIG. 17 depicts a front view of an exemplary "V" shaped staple having a hinge feature.

FIG. 17 depicts an exemplary staple (690), which can replace staple (190) or (90) in the plurality of staples. Staple (690) includes crown (696) and a pair of legs (698). Crown (696) includes two straight portions (697) and a hinge feature (695). Hinge feature (695) in the present example is located between each of straight portions (697) and is formed as two interlocking rings or loops (691, 692). In the undeployed state as shown in FIG. 17, staple (690) defines an angle (α4) between straight portions (697), and staple (690) defines a distance (d4) between legs (698). After deployment and after staple (690) is subject to tension from tissue forces as described above, staple (690) expands about hinge feature (695) such that angle (α4) increases, which also corresponds with an increase in distance (d4). This produces a broader "V" shape for staples (690) that resembles staples (690) becoming closer to linear shaped.

In the present example, hinge feature (695) is configured such that it is operable to change the orientation of staple (690) depending on the forces staple (690) is subjected to. Also in the present example, hinge feature (695) is configurable such that a tension within hinge feature (695) can be such that a threshold amount of force must be imparted upon hinge feature (695) to cause staple (690) to change configuration as described above. For instance, in one version the amount of contact between interlocking rings (691, 692) can be configured to provide greater or lesser friction among these components, thereby making hinge feature (695) more or less responsive to a given force applied on staple (690). Other ways to configure the tension with hinge feature (695) will be apparent to those of ordinary skill in the art in view of the teachings herein.

Staple (690) can be considered to define a first portion that includes one leg (698) and one portion (697) of crown (696), and a second portion that includes the other leg (698) and the other portion (697) of crown (696). In this manner, first and second portions of staple (690) are connected at hinge feature (695) and are operable to move relative to one another about hinge feature (695) depending on the forces being exerted on the first and second portions of staple (690). In some instances, a force may be exerted evenly on staple (690) such that each of the first and second portions of staple (690) experience the same force and move relative to one another in a similar fashion. In some other instances, a different degree of force may act on each of the first and second portions of staple (690). In such examples, the degree of movement of the first and the second portions of staple (690) may differ. For example, the portion of staple (690) experiencing the larger force may move a greater distance radially compared to the other portion of staple (690) experiencing the lower force.

As shown in FIG. 17, hinge feature (695) is coplanar with crown (696). Additionally, legs (698) extend generally orthogonal to a plane defined by crown (696) and hinge feature (695). In use after deployment of staples (690), tension from radial tissue forces act on staple (690) and such forces are generally orthogonal to axes defined by legs (698) when in the unformed state. Accordingly, in this manner, hinge feature (695) is configured and oriented so that when radial tissue forces act on staple (690), expansion of staple (690) occurs as described above. While the above examples describe expansion of staple (690), in some instances, hinge feature (695) also allows for staple (690) to move or change orientation from an expanded state to a more retracted or compact state. This could be the case when forces acting on staple (690) subside. Of course, in such examples hinge feature (695) can be configured to allow for expansion only without the ability to contract or close down to a smaller width. In view of the teachings herein, other ways to configure staple (690) with hinge feature (695) will be apparent to those of ordinary skill in the art.

Figure 18:
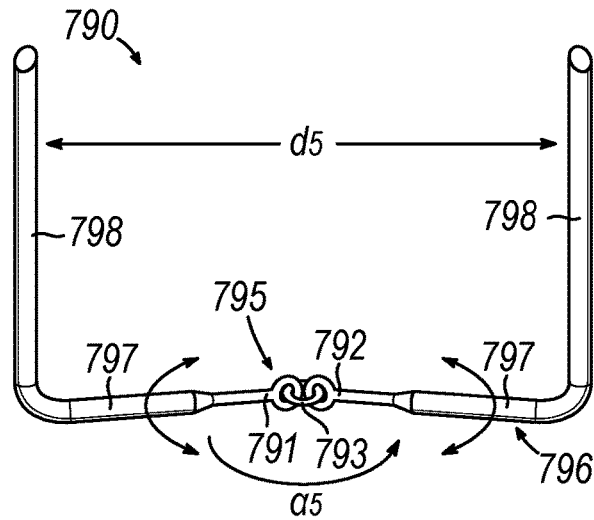
FIG. 18 depicts a front view of an exemplary "V" shaped staple having an alternate hinge feature.

FIG. 18 depicts an exemplary staple (790), which can replace staple (190) or (90) in the plurality of staples. Staple (790) includes crown (796) and a pair of legs (798). Crown (796) includes two straight portions (797) and a hinge feature (795). Hinge feature (795) in the present example is located between each of straight portions (797) and is formed as two interlocking rings or loops (791, 792) with an intermediate member or link (793). In the undeployed state as shown in FIG. 18, staple (790) defines an angle (α5) between straight portions (797), and staple (790) defines a distance (d5) between legs (798). After deployment and after staple (790) is subject to tension from tissue forces as described above, staple (790) expands about hinge feature (795) such that angle (α5) increases, which also corresponds with an increase in distance (d5). This produces a broader "V" shape for staples (790) that resembles staples (790) becoming closer to linear shaped.

In the present example, hinge feature (795) is configured such that it is operable to change the orientation of staple (790) depending on the forces staple (790) is subjected to. Also in the present example, hinge feature (795) is configurable such that a tension within hinge feature (795) can be such that a threshold amount of force must be imparted upon hinge feature (795) to cause staple (790) to change configuration as described above. For instance, in one version the amount of contact between interlocking rings (791, 792) and intermediate member (793) can be configured to provide greater or lesser friction among these components, thereby making hinge feature (795) more or less responsive to a given force applied on staple (790). Other ways to configure the tension with hinge feature (795) will be apparent to those of ordinary skill in the art in view of the teachings herein.

Staple (790) can be considered to define a first portion that includes one leg (798) and one portion (797) of crown (796), and a second portion that includes the other leg (798) and the other portion (797) of crown (796). In this example each of these first and second portions connect with intermediate member (793). In this manner, first and second portions of staple (790) are connected at hinge feature (795) and are operable to move relative to one another about hinge feature (795) depending on the forces being exerted on the first and second portions of staple (790). In some instances, a force may be exerted evenly on staple (790) such that each of the first and second portions of staple (790) experience the same force and move relative to one another in a similar fashion. In some other instances, a different degree of force may act on each of the first and second portions of staple (790). In such examples, the degree of movement of the first and the second portions of staple (790) may differ. For example, the portion of staple (790) experiencing the larger force may move a greater distance radially compared to the other portion of staple (790) experiencing the lower force.

As shown in FIG. 18, hinge feature (795) is coplanar with crown (796). Additionally, legs (798) extend generally orthogonal to a plane defined by crown (796) and hinge feature (795). In use after deployment of staples (790), tension from radial tissue forces act on staple (790) and such forces are generally orthogonal to axes defined by legs (798) when in the unformed state. Accordingly, in this manner, hinge feature (795) is configured and oriented so that when radial tissue forces act on staple (790), expansion of staple (790) occurs as described above. While the above examples describe expansion of staple (790), in some instances, hinge feature (795) also allows for staple (790) to move or change orientation from an expanded state to a more retracted or compact state. This could be the case when forces acting on staple (790) subside. Of course, in such examples hinge feature (795) can be configured to allow for expansion only without the ability to contract or close down to a smaller width. In view of the teachings herein, other ways to configure staple (790) with hinge feature (795) will be apparent to those of ordinary skill in the art.

5. Exemplary Expandable Staples with "V" Shaped Crown and Cable

Figure 19:
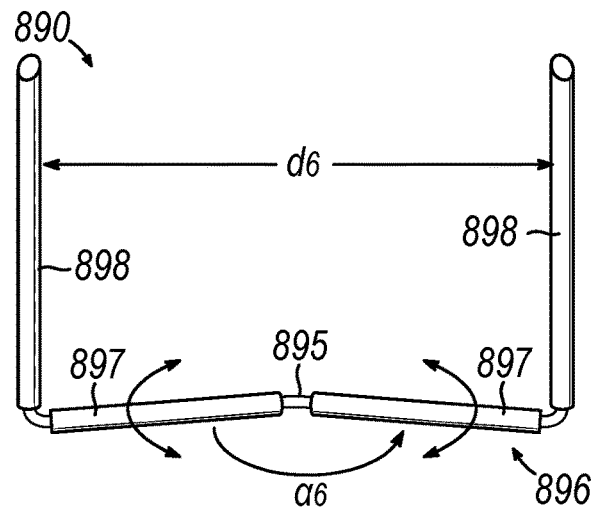
FIG. 19 depicts a front view of an exemplary "V" shaped staple having a cable connecting portions of a crown of the staple.

FIG. 19 depicts an exemplary staple (890), which can replace staple (190) or (90) in the plurality of staples. Staple (890) includes crown (896) and a pair of legs (898). Crown (896) includes two straight portions (897) and a cable (895). Cable (895) in the present example extends from one leg (898), through straight portions (897), to the other leg (898). In the present example, cable (895) is configured as a unitary cable structure, while in other examples cable feature (895) is configured as multiple discrete sections of cable structure that join or connect two portions of staple (890). In the present example, cable (895) is present where each leg (898) meets or connects with a respective straight portion (897). In some other versions, cable (895) is omitted here such that cable (895) is present only in the middle portion of staple (890) connecting straight portions (897).

In the undeployed state as shown in FIG. 19, staple (890) defines an angle (α6) between straight portions (897), and staple (890) defines a distance (d6) between legs (898). After deployment and after staple (890) is subject to tension from tissue forces as described above, staple (890) expands in width by bending cable (895) such that angle (α6) increases, which also corresponds with an increase in distance (d6). This produces a broader "V" shape for staples (890) that resembles staples (890) becoming closer to linear shaped.

In the present example, cable (895) is configured such that it is operable to change the orientation of staple (890) depending on the forces staple (890) is subjected to. Also in the present example, cable (895) is configurable such that a tension within cable (895) can be such that a threshold amount of force must be imparted upon cable (895) to cause staple (890) to change configuration as described above. For instance, in one version the amount of contact between cable (895) and straight portions (897) through which cable (895) passes can be configured to provide greater or lesser friction among these components, thereby making staple (890) more or less responsive to a given force applied on staple (890). Other ways to configure the tension with cable (895) will be apparent to those of ordinary skill in the art in view of the teachings herein. For instance, the rigidity of cable (895) can be configured based on the material, construction, or diameter of cable (895).

Staple (890) can be considered to define a first portion that includes one leg (898) and one portion (897) of crown (896), and a second portion that includes the other leg (898) and the other portion (897) of crown (896). In this manner, first and second portions of staple (890) are connected by cable (895) and are operable to move relative to one another about cable (895) depending on the forces being exerted on the first and second portions of staple (890). In some instances, a force may be exerted evenly on staple (890) such that each of the first and second portions of staple (890) experience the same force and move relative to one another in a similar fashion. In some other instances, a different degree of force may act on each of the first and second portions of staple (890). In such examples, the degree of movement of the first and the second portions of staple (890) may differ. For example, the portion of staple (890) experiencing the larger force may move a greater distance radially compared to the other portion of staple (890) experiencing the lower force.

As shown in FIG. 19, cable (895) is coplanar with crown (896). Additionally, legs (898) extend generally orthogonal to a plane defined by crown (896) and cable (895). In use after deployment of staples (890), tension from radial tissue forces act on staple (890) and such forces are generally orthogonal to axes defined by legs (898) when in the unformed state. Accordingly, in this manner, cable (895) is configured and oriented so that when radial tissue forces act on staple (890), expansion of staple (890) occurs as described above. While the above examples describe expansion of staple (890), in some instances, cable (895) also allows for staple (890) to move or change orientation from an expanded state to a more retracted or compact state. This could be the case when forces acting on staple (890) subside. Of course, in such examples cable (895) can be configured to allow for expansion only without the ability to contract or close down to a smaller width. In view of the teachings herein, other ways to configure staple (890) with cable (895) will be apparent to those of ordinary skill in the art.

B. Exemplary Staple Patterns for Staples with "V" Shaped Crowns

Another variable for consideration with expandable staples is staple pattern. The staple pattern pertains to the arrangement and spacing of the staples. FIGS. 20A-20E illustrate staple patterns that may be used or adapted for use in a circular staple configuration and with expandable staples, such as staples (190, 290, 390, 490, 590, 690, 790, 890) described above.

Figure 20A:
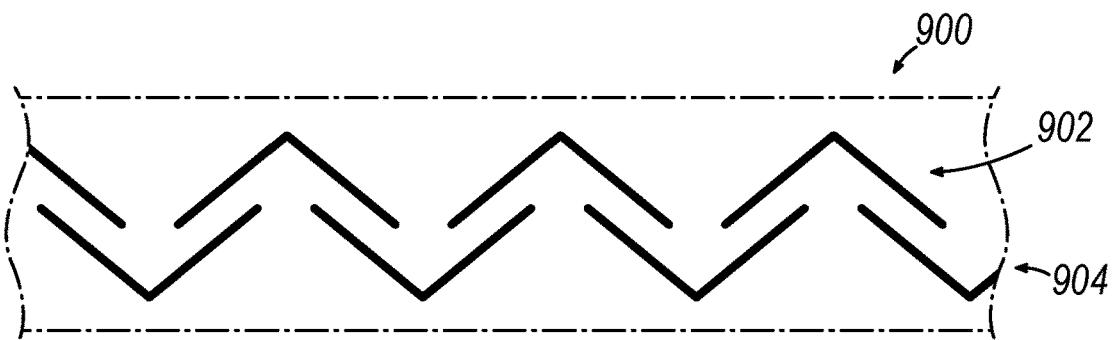

FIG. 20A illustrates an exemplary staple pattern (900) for "V" shaped staples with equal length arms. As used herein, the "arms" of a "V" shaped staple is understood to refer to the distance along the crown portion from a given staple leg to the vertex. While FIG. 20A depicts staple pattern (900) in a linear pattern, this pattern (900) is adaptable into a wrap-around staple pattern for a circular stapler application. For instance, with a circular stapler, the staples may differ in size and/or shape between the inner row and outer row, although they could be of the same size and/or shape in some versions.

With staple pattern (900), there is a first row or outer row (902) of staples and a second row or inner row (904) of staples. As shown, the staples of first row (902) are opposite facing and offset from the staples of second row (904). This offset appears as a lateral offset in pattern (900), and this offset appears as a circumferential offset when pattern (900) is in a circular or wrap-around staple pattern as seen in FIGS. 8-12. Furthermore, in the present example the opposite facing arrangement is shown with the staples in outer row (902) have the vertex oriented to point outward, while the staples in inner row (904) have the vertex oriented to point inward.

As evident from FIGS. 8-12 and FIG. 20A, with pattern (900), the staples can move from their initial "V" shape to an expanded "V" shape without the staples interfering with one another. As shown in FIGS. 8-12, pattern (900) allows for outward radial expansion of a circular staple pattern when the staples undergo expansion as described above.

Figure 20B:

FIG. 20B illustrates another exemplary staple pattern (1000) for "V" shaped staples with equal length arms. FIG. 20B depicts staple pattern (1000) as a linear pattern; however, this pattern (1000) is adaptable into a wrap-around staple pattern for a circular stapler application similar to pattern (900) as described above.

With staple pattern (1000), there is a first row or outer row (1002) of staples and a second row or inner row (1004) of staples. As shown, the staples of first row (1002) are opposite facing and offset from the staples of second row (1004). This offset appears as a lateral offset in pattern (1000), and this offset appears as a circumferential offset when pattern (1000) is in a circular or wrap-around staple pattern. Furthermore, in the present example the opposite facing arrangement is shown with the staples in outer row (1002) have the vertex oriented to point inward, while the staples in inner row (1004) have the vertex oriented to point outward. With pattern (1000), the staples can move from their initial "V" shape to an expanded "V" shape without the staples interfering with one another. Furthermore, pattern (1000) allows for outward radial expansion of a circular staple pattern when the staples undergo expansion as described above.

Figure 20C:
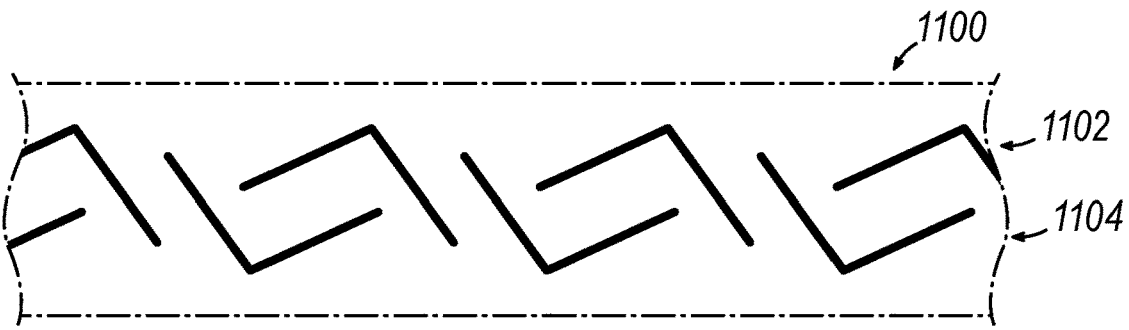

FIG. 20C illustrates another exemplary staple pattern (1100) for "V" shaped staples with equal length arms. FIG. 20C depicts staple pattern (1100) as a linear pattern; however, this pattern (1100) is adaptable into a wrap-around staple pattern for a circular stapler application similar to pattern (900) as described above.

With staple pattern (1100), there is a first row or outer row (1102) of staples and a second row or inner row (1104) of staples. As with pattern (900), with pattern (1100), the staples of outer row (1102) have their vertex generally pointing outward while the staples of inner row (1104) have their vertex generally pointing inward. Moreover, pattern (1100) has staple rows (1102, 1104) with staples that are canted in order to stagger the anchor points between the staple and the tissue to not be parallel to the staple line. This canted arrangement for staples also increases the rigid-body rotation of the staples independent of their flexure. In this manner, pattern (1100) provides for a stapling arrangement with less stress on the tissue for a given amount of elongation of the staple line compared to at least some other stapling patterns. As with the other patterns, with pattern (1100) the staples can move from their initial "V" shape to an expanded "V" shape without the staples interfering with one another. Furthermore, pattern (1100) allows for outward radial expansion of a circular staple pattern when the staples undergo expansion as described above.

Figure 20D:
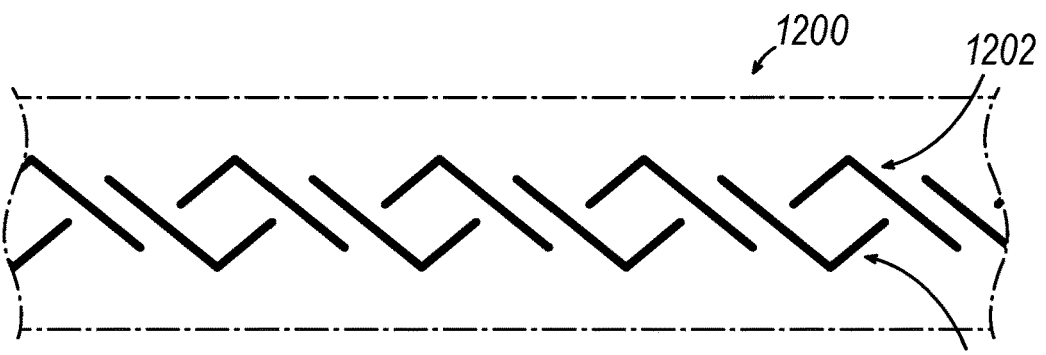

FIG. 20D illustrates another exemplary staple pattern (1200) for "V" shaped staples with unequal length arms. FIG. 20D depicts staple pattern (1200) as a linear pattern; however, this pattern (1200) is adaptable into a wrap-around staple pattern for a circular stapler application similar to pattern (900) as described above.

With staple pattern (1200), there is a first row or outer row (1202) of staples and a second row or inner row (1204) of staples. As shown, the staples of first row (1202) are opposite facing and offset from the staples of second row (1204). This offset appears as a lateral offset in pattern (1200), and this offset appears as a circumferential offset when pattern (1200) is in a circular or wrap-around staple pattern. Furthermore, in the present example the opposite facing arrangement is shown with the staples in outer row (1202) have the vertex oriented to point outward, while the staples in inner row (1004) have the vertex oriented to point inward. With pattern (1200), the staples can move from their initial "V" shape to an expanded "V" shape without the staples interfering with one another. Furthermore, pattern (1200) allows for outward radial expansion of a circular staple pattern when the staples undergo expansion as described above.

FIG. 20E illustrates another exemplary circular staple pattern (1300) for alternating angled staples (1302) with straight crowns and staples (1304) with "V" shaped crowns. With staple pattern (1300), staples (1304) with "V" shaped crowns alternate circumferentially with the vertex a staple (1304) pointing outwardly and then the adjacent staple (1304) oriented with the vertex pointing inwardly. Furthermore, between each staple (1304) is one of staples (1302). Staples (1302) alternate circumferentially in their angle direction as shown. With this arrangement, the combined staples (1302, 1304) define a pattern (1300) that forms a "W" shape repeating circumferentially. With pattern (1300), staples (1304) can move from their initial "V" shape to an expanded "V" shape without interfering with staples (1302) having the straight crowns. Furthermore, pattern (1300) allows for outward radial expansion of a circular staple pattern when the staples undergo expansion as described above.

C. Exemplary Stapling Head Assembly with Staples Having Crown Elongation Features FIGS. 21A-23B illustrate exemplary expandable staples that incorporate one or more features into the crown portion that enable the staples to elongate or expand after being deployed and when the staples are subjected to tissue forces.

1. Exemplary Staples with Bent Crowns

FIGS. 21A and 21B depict staple (990) that is expandable and includes elongation feature (995). In the present example, staple (990) comprises legs (998) that are shown formed into a "B" shape for fastening tissue and oriented in a coplanar fashion. Staple (990) further comprises crown (996) that incorporates elongation feature (995). In the present example, elongation feature (995) comprises a bend having an angled or "V" shape that is located along a middle portion of crown (996). In the illustrated example, elongation feature (995) extends along a plane that is generally orthogonal to the plane encompassing legs (998). With this configuration, elongation feature (995) maintains legs (998) in a coplanar orientation while enabling staple (990) to expand laterally such that its width increases during staple expansion as shown by staple width (D1) in the initial state shown in FIG. 21A compared to staple width (D2) in the expanded state shown in FIG. 21B.

Staple (990) transitions or moves from its initial state shown in FIG. 21A to its expanded state shown in FIG. 21B based on tissue forces acting on staple (990) after staples (990) have been deployed in making the anastomosis. For instance, after the anastomosis tissue may try to expand due to peristalsis or based on objects passing through the lumen created by the anastomosis. In response, a force is exerted on staples (990) that pulls legs (998) apart from one another. With elongation feature (995) of crown (996), staples (990) can expand in width by the bend of elongation feature (995) straightening out due to the tissue forces acting on staple (990). This in turn can also promote maintaining the formed state of legs (998) to ensure adequate tissue fastening. While elongation feature (995) is shown and described as an angled bend having a "V" shape, in view of the teachings herein, other configurations for elongation feature (995) will be apparent to those of ordinary skill in the art.

2. Exemplary Staples with Crown Sliding Feature

Figure 22A:
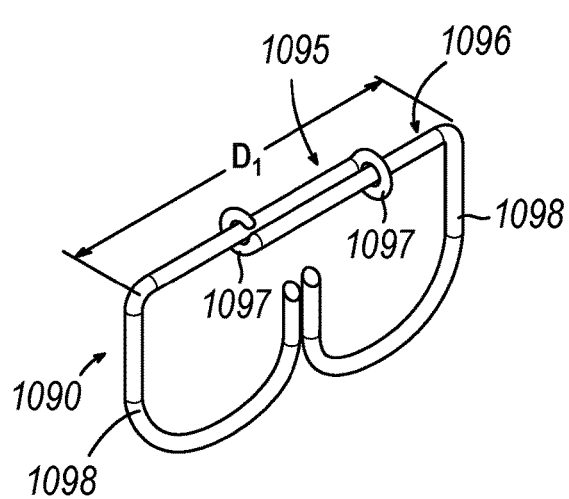
FIG. 22A depicts a perspective view of an exemplary staple having a crown with an expandable sliding feature, shown in a relaxed state.
Figure 22B:
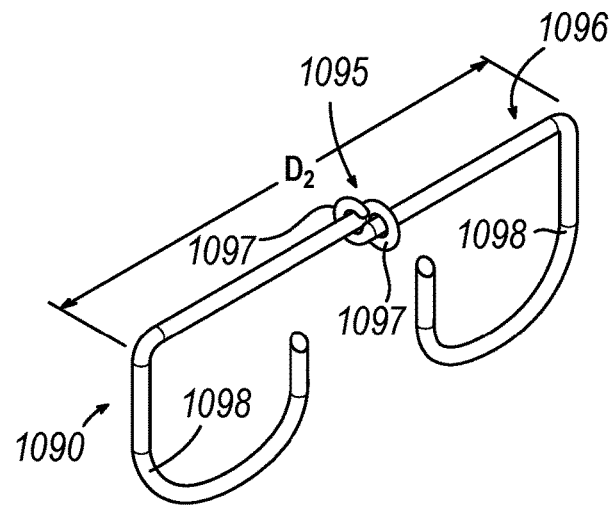
FIG. 22B depicts a perspective view of the staple of FIG. 22A, shown in an expanded state.

FIGS. 22A and 22B depict staple (1090) that is expandable and includes elongation feature (1095). In the present example, staple (1090) comprises legs (1098) that are shown formed into a "B" shape for fastening tissue and oriented in a coplanar fashion. Staple (1090) further comprises crown (1096) that incorporates elongation feature (1095). In the present example, elongation feature (1095) comprises a sliding or slidable feature that is located along a middle portion of crown (1096) and includes two linking members (1097) that in the present example are formed by bends in the staple wire. Linking members (1097) extend parallel to one another and are slidable relative to each other based on tissue forces acting on staple (1090). With this configuration, elongation feature (1095) maintains legs (1098) in a coplanar orientation while enabling staple (1090) to expand laterally such that its width increases during staple expansion as shown by staple width (D1) in the initial state shown in FIG. 22A compared to staple width (D2) in the expanded state shown in FIG. 22B.

Staple (1090) transitions or moves from its initial state shown in FIG. 22A to its expanded state shown in FIG. 22B based on tissue forces acting on staple (1090) after staples (1090) have been deployed in making the anastomosis. For instance, after the anastomosis, tissue may try to expand due to peristalsis or based on objects passing through the lumen created by the anastomosis. In response, force is exerted on staples (1090) that pulls legs (1098) apart from one another. With elongation feature (1095) of crown (1096), staples (1090) can expand in width by the slidable nature of linking members (1097) when the tissue forces act on staple (1090). For instance, FIG. 22A illustrates staple (1090) in its initial state, while FIG. 22B illustrates staple (1090) in its expanded state. This in turn can also promote maintaining the formed state of legs (1098) to ensure adequate tissue fastening, while still allowing for staple expansion. In view of the teachings herein, other configurations for elongation feature (1095) will be apparent to those of ordinary skill in the art.

3. Exemplary Staples with Crown Coil Feature

Figure 23A:
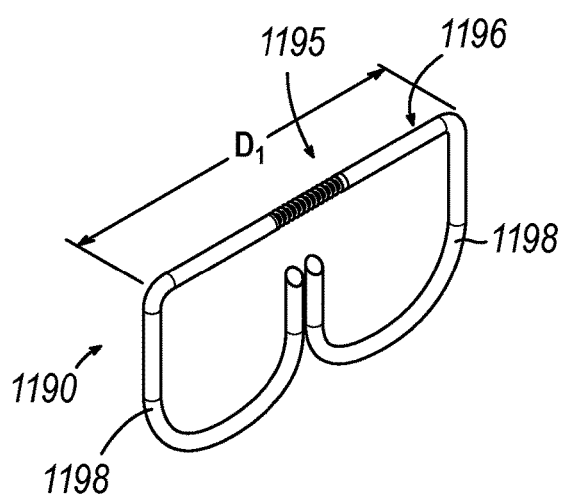
FIG. 23A depicts a perspective view of an exemplary staple having a crown with an expandable coil feature, shown in a relaxed state.
Figure 23B:
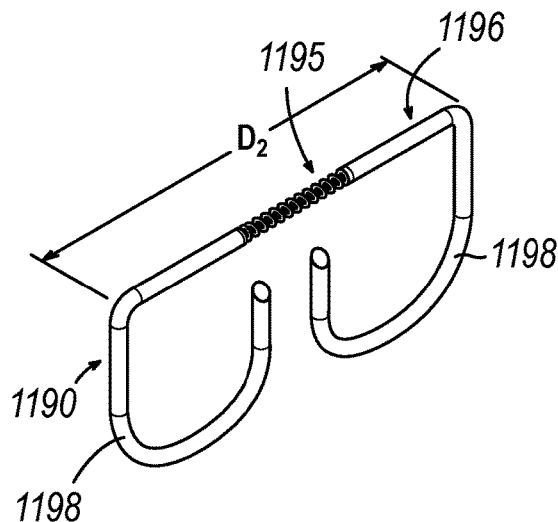
FIG. 23B depicts a perspective view of the staple of FIG. 23A, shown in an expanded state.

FIGS. 23A and 23B depict staple (1190) that is expandable and includes elongation feature (1195). In the present example, staple (1190) comprises legs (1198) that are shown formed into a "B" shape for fastening tissue and oriented in a coplanar fashion. Staple (1190) further comprises crown (1196) that incorporates elongation feature (1195). In the present example, elongation feature (1195) comprises a coil feature that is located along a middle portion of crown (1196) and formed within a portion of crown (1196). With this configuration, elongation feature (1195) maintains legs (1198) in a coplanar orientation while enabling staple (1190) to expand laterally such that its width increases during staple expansion as shown by staple width (D1) in the initial state shown in FIG. 23A compared to staple width (D2) in the expanded state shown in FIG. 23B.

Staple (1190) transitions or moves from its initial state shown in FIG. 23A to its expanded state shown in FIG. 23B based on tissue forces acting on staple (1190) after staples (1190) have been deployed in making the anastomosis. For instance, after the anastomosis, tissue may try to expand due to peristalsis or based on objects passing through the lumen created by the anastomosis. In response, force is exerted on staples (1190) that pulls legs (1198) apart from one another. With elongation feature (1195) of crown (1196), staples (1190) can expand in width by plastically deforming the coil feature when the tissue forces act on staple (1190). For instance, FIG. 23A illustrates staple (1190) in its initial state, while FIG. 23B illustrates staple (1190) in its expanded state. This in turn can also promote maintaining the formed state of legs (1198) to ensure adequate tissue fastening, while still allowing for staple expansion. In view of the teachings herein, other configurations for elongation feature (1195) will be apparent to those of ordinary skill in the art.

D. Exemplary Stapling Head Assembly with Staples Having Curved Crowns

In some other versions of instrument (10), stapling head assemblies (300, 600) can be adapted for use with alternate configured staples. For instance, in one example, assemblies (300, 600) can be adapted for use with staples having curved crowns. In view of the teachings herein, such adaptations of stapling head assemblies (300, 600) will be apparent to those of ordinary skill in the art. The following sections will describe various exemplary staples having curved crowns.

FIGS. 24-27 depicts an exemplary staple (1290) comprising legs (1298) and a crown (1296). As shown, legs (1298) are formed and fasten two tissue structures (T1, T2) together. Crown (1296) is formed of two straight portions (1297) connected by alternating and repeating curved portions (1295). In the present example, additional straight portions (1299) connect repeating curved portions (1295). In some other versions, straight portions (1299) may be omitted. As seen in FIG. 25, additional straight portions (1299), when present, provide a way to increase the height (H) of staple (1290). With staples (1290), it can also be understood that two connected curved portions (1295), whether connected by straight portion (1299) or not, can form and "S" shape. In this manner, staple (1290) can also be considered as having crown (1296) with a repeating "S" shape.

FIGS. 26 and 27 depict a respective side view and front view of staple (1290) with tissues (T1, T2). These figures show an unbent portion of one of legs (1298) and its connection with crown (1296). These figures further show the formed or bent portions of legs (1298) wrapped around the tissue assembly. With crown (1296) on one side of tissues (T1, T2) contacting tissue (T1), and formed leg (1298) on the opposite side of tissues (T1, T2) contacting tissue (T2), staple (1290) securely fastens tissues (T1, T2) together as shown.

Figure 28:
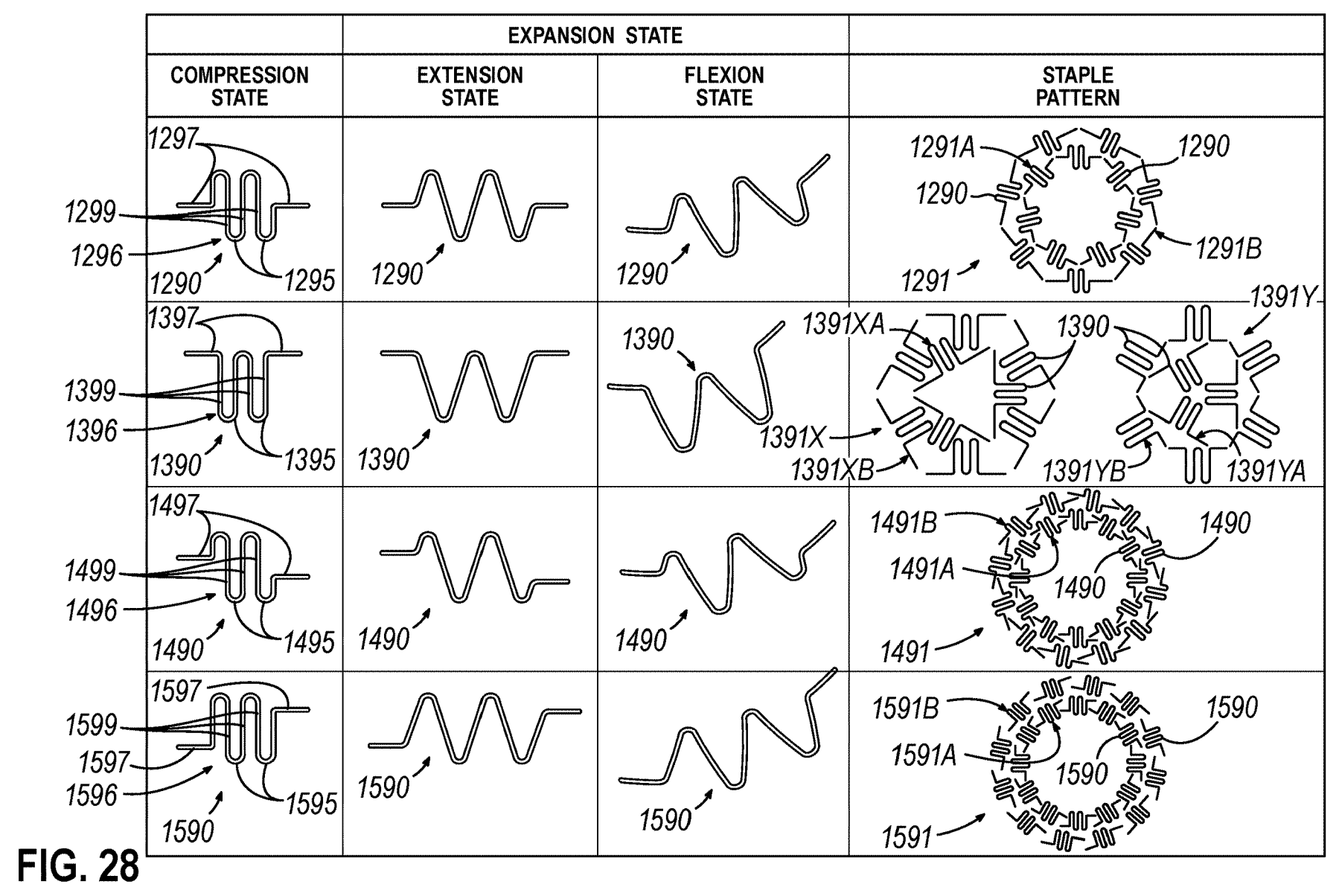

Referring to FIG. 28, various states or conditions are depicted for staples that include curved-shaped crowns. For instance, staple (1290) is shown in a compression state and two expansion states: an extension state and a flexion state. In one versions of staple (1290), the compression state represents the initial formed staple configuration where staple (1290) is not subjected to tissue forces. This can be considered the relaxed state for staple (1290) in such a version. In another version of staple (1290), the compression state can represent a formed staple configuration where staple (1290) is under a compressive tension. For instance, in such a version, staple (1290) may be loaded into instrument (10) under this compressive tension such that after deployment, staple (1290) automatically adopts the extension state without the need for tissue forces acting on staple (1290). In the version where the compression state coincides with a relaxed state, staple (1290) expands to the extension state based on tissue forces acting on staple (1290) as described above, and in response staple (1290) expands as shown in the extension state.

Another expansion state depicted in FIG. 28 for staple (1290) is the flexion state. Once staple (1290) has been deployed and undergone extension due to either relieving pre-formed tension or reacting to tissue forces acting on staple (1290) as mentioned above, based on tissue forces acting on staple (1290), staple (1290) can move to the flexion state. In the present example, the multiple curved-shape portions of crown (1296) provide for a curved flexion state as shown. This can be beneficial when considering the desire to expand the diameter of the anastomosis as it can aid in allowing expansion while not putting excessive tension on the stapled tissue thereby promoting the integrity of the seal at the anastomosis.

FIG. 28 additionally depicts an exemplary staple pattern (1291) for use with staples (1290). Staple pattern (1291) comprises an inner ring of staples (1291A) and an outer ring of staples (1291B) each formed using staples (1290) as shown. In use after deployment, staples (1290) arranged in staple pattern (1291), provides for an anastomosis where staples (1290) can expand and flex to produce an anastomosis having an initial diameter and a subsequent diameter that is larger than the initial diameter. This allows the lumen created by the anastomosis to achieve a size that is closer to the original size of the severed lumens joined by the anastomosis.

FIG. 28 depicts additional exemplary staples (1390, 1490, 1590) each comprising respective legs and a respective crown (1396, 1496, 1596). In these examples, the legs of staples (1390, 1490, 1590) are configured the same as legs (1298) of staple (1290). Accordingly, the description of legs (1298) applies equally to staples (1390, 1490, 1590) with the legs configured to fasten two tissue structures (T1, T2) together as described above.

With staple (1390), crown (1396) is formed of two straight portions (1397) connected by alternating and repeating curved portions (1395) that form a "W" shape. In the present example, additional straight portions (1399) connect repeating curved portions (1395) providing an increase in the height of staple (1390).

With staple (1490), crown (1496) is formed of two offset straight portions (1497) connected by alternating and repeating curved portions (1495) with additional straight portions (1499) connecting repeating curved portions (1495). Staple (1490) is similar in configuration to staple (1290), with the offset of straight portions (1497) being a difference. With staple (1290), straight portions (1297) are oriented along the same axis that intersects a centerline of the height defined by crown (1296). However, with staple (1490), straight portions (1497) are offset with one positioned above a centerline of the height defined by crown (1496), and one positioned below the centerline of the height defined by crown (1496).

With staple (1590), crown is formed of two offset straight portions (1597) connected by alternating and repeating curved portions (1595). Staple (1590) is similar in configuration to staple (1290), with the offset of straight portions (1597) being a difference. With staple (1290), straight portions (1297) are oriented along the same axis that intersects a centerline of the height defined by crown (1296). However, with staple (1590), straight portions (1597) are offset with one positioned above a centerline of the height defined by crown (1596), and one positioned below the centerline of the height defined by crown (1596). This configuration is similar to staple (1490); however, the difference between staples (1490) and staple (1590) is that the offset of straight portions (1597) is opposite to the arrangement shown for straight portions (1497) of staple (1490). For instance, where a straight portion (1497) of staple (1490) may be above a centerline of the staple height defined by crown (1496), with staple (1590) the corresponding straight portion (1597) would be below a centerline of the staple height defined by crown (1596).

Referring to FIG. 28, various states or conditions are depicted for staples (1390, 1490, 1590) that include curved-shaped crowns. For instance, staples (1390, 1490, 1590) are shown in a compression state and two expansion states: an extension state and a flexion state. In one versions of staples (1390, 1490, 1590), the compression state represents the initial formed staple configuration where staples (1390, 1490, 1590) are not subjected to tissue forces. This can be considered the relaxed state for staples (1390, 1490, 1590) in such versions. In another version of staples (1390, 1490, 1590), the compression state can represent a formed staple configuration where staples (1390, 1490, 1590) are under a compressive tension. For instance, in such versions, staples (1390, 1490, 1590) may be loaded into instrument (10) under this compressive tension such that after deployment, staples (1390, 1490, 1590) automatically adopt the extension state without the need for tissue forces acting on staples (1390, 1490, 1590). In the version where the compression state coincides with a relaxed state, staples (1390, 1490, 1590) expand to the extension state based on tissue forces acting on staples (1390, 1490, 1590) as described above, and in response staples (1390, 1490, 1590) expand as shown in the extension state.

Another expansion state depicted in FIG. 28 for staples (1390, 1490, 1590) is the flexion state. Once staples (1390, 1490, 1590) have been deployed and undergone extension due to either relieving pre-formed tension or reacting to tissue forces acting on staples (1390, 1490, 1590) as mentioned above, based on tissue forces acting on staples (1390, 1490, 1590), staples (1390, 1490, 1590) can move to the flexion state. In the present example, the multiple curved-shape portions of crowns (1396, 1496, 1596) provide for a curved flexion state as shown. This can be beneficial when considering the desire to expand the diameter of the anastomosis as it can aid in allowing expansion while not putting excessive tension on the stapled tissue thereby promoting the integrity of the seal at the anastomosis.

FIG. 28 additionally depicts exemplary staple patterns (1391X, 1391Y, 1491, 1591) for use with respective staples (1390, 1490, 1590). Staple patterns (1391X, 1391Y, 1491, 1591) each comprise an inner ring of staples (1391XA, 1391YA, 1491A, 1591A) and an outer ring of staples (1391YB, 1391YB, 1491B, 1591B) each formed using respective staples (1390, 1490, 1590) as shown. In use after deployment, staples (1390, 1490, 1590) arranged in respective staple patterns (1391X, 1391Y, 1491, 1591), provide for an anastomosis where staples (1390, 1490, 1590) can expand and flex to produce an anastomosis having an initial diameter and a subsequent diameter that is larger than the initial diameter. This allows the lumen created by the anastomosis to achieve a size that is closer to the original size of the severed lumens joined by the anastomosis.

E. Exemplary Nested "S" and "C" Shaped Expandable Staples

Figure 29A:
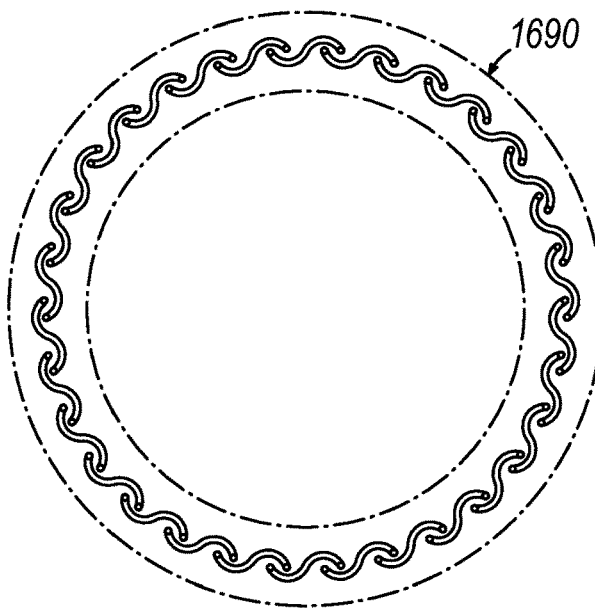
FIG. 29A depicts a top view of exemplary "S" shaped staples in a horizontal nested arrangement in a relaxed state.
Figure 29B:
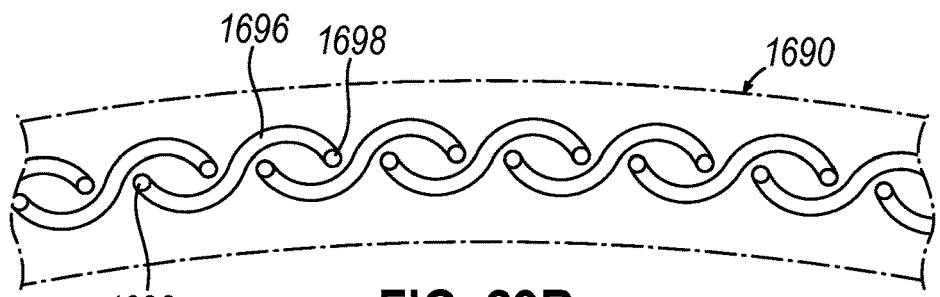
FIG. 29B depicts an enlarged view of the staples of FIG. 29A.

FIGS. 29A-29D depict another exemplary expandable staple (1690). Staples (1690) are configured with "S" shaped crowns (1696) and straight legs (1698). As shown in FIGS. 29A and 29B, staples (1690) are configured in a horizontal nested pattern with each "S" shaped staple (1690) overlapping adjacent staples (1690). In this manner, the resultant staple pattern closes any gaps in the circular staple pattern with a single row of staples (1690).

Figure 29C:
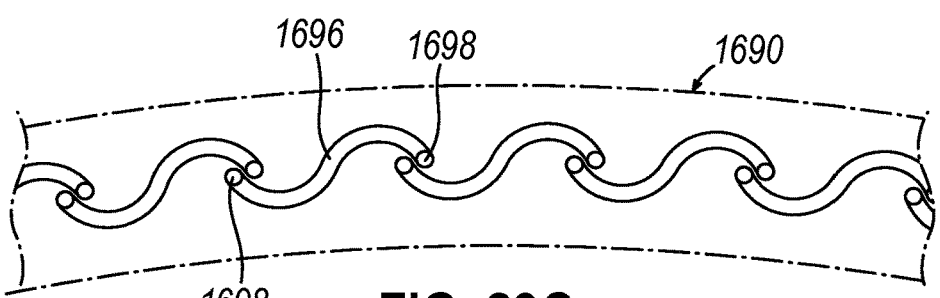
FIG. 29C depicts the staples of FIG. 29B, showing the nested arrangement in an expanded state.
Figure 29D:
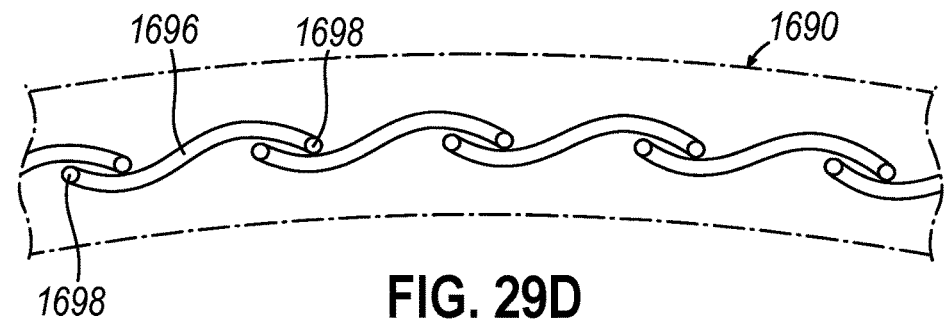
FIG. 29D depicts the staples of FIG. 29C, showing the staples themselves in an expanded state.

While FIGS. 29A and 29B illustrate a relaxed state of the nested arrangement of staples (1690), FIG. 29C depicts an expanded state where the nested arrangement of staples (1690) allows for expansion of the staple line in response to tissue expansion forces acting on staples (1690). More specifically, as tissue forces act on staples (1690) in their nested arrangement, staples (1690) reorient their relative position such that the nesting arrangement becomes less such that the overlapping of staples (1690) decreases when the pattern expands. Furthermore, in some versions as shown in FIG. 29D, staples (1690) can also provide for expansion by staples (1690) themselves expanding in similar ways as described above. In this manner, expansion of the staple line creating the anastomosis can be achieved in two ways: by the nesting pattern expanding, and/or by staples (1690) themselves expanding.

Figure 30:
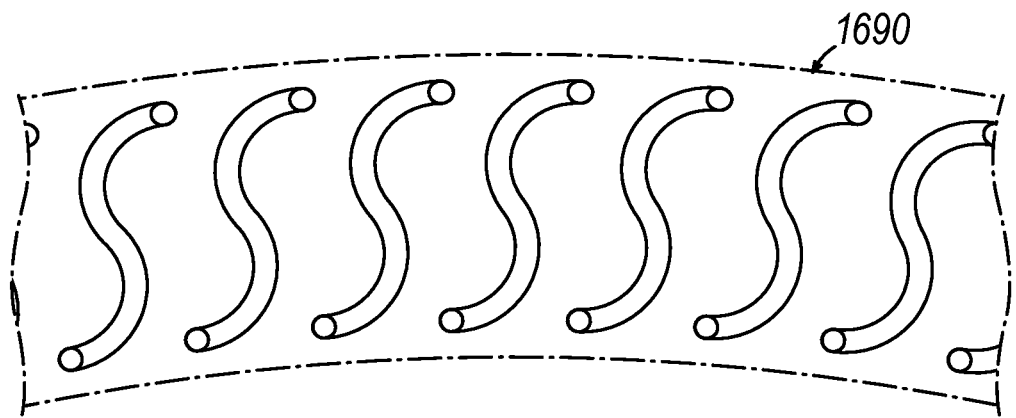
FIG. 30 depicts a top view of exemplary "S" shaped staples in a slightly angled nested arrangement in a relaxed state.

FIG. 30 depicts another exemplary orientation for staples (1690), where "S" shaped staples (1690) are oriented in a slightly angled and nested arrangement or configuration. Similar to the configuration shown in FIGS. 29A-D, staples (1690) configured in this manner may similarly allow for expansion where staples (1690) reorient their nested positions and the nesting degree in response to tissue forces acting on staples (1690). By way of example only, and not limitation, the nesting arrangement shown in FIG. 30 may adopt further spacing between staples (1690) when moving from the relaxed state shown in FIG. 30 to an expanded state. Still yet, in some versions when moving to the expanded state staples (1690) may pivot or rotate to some degree—taking on a more horizontal arrangement—when subjected to tissue expansive forces. Additionally, like shown in FIG. 29D, in some versions where staples (1690) are configured as shown in FIG. 30, staples (1690) themselves may also expand becoming more linear in their crown shape as seen in FIG. 29D.

Figure 31:
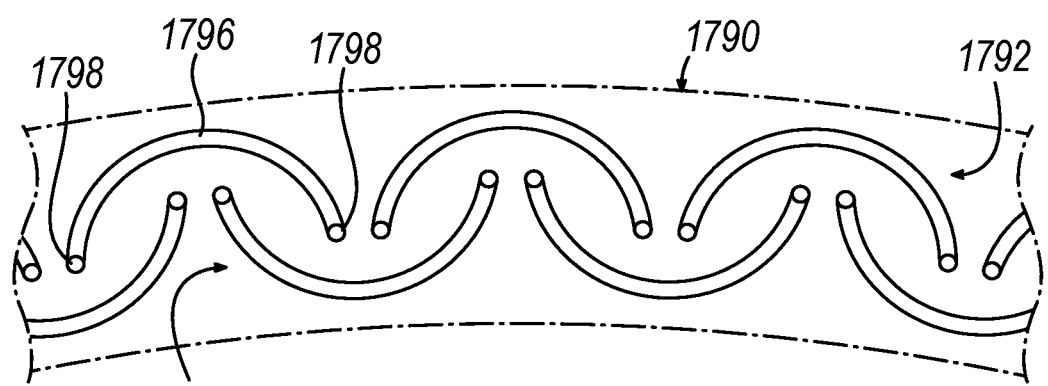
FIG. 31 depicts a top view of exemplary "C" shaped staples in a two-row nested arrangement.

FIG. 31 depicts another exemplary expandable staple (1790). Staples (1790) are configured with "C" shaped crowns (1796) and straight legs (1798). Staples (1790) are configured in a horizontal nested pattern with an outer row (1792) of staples (1790) opening inward toward a center of the circular staple pattern, and an inner row (1794) of staples (1790) opening outward away from a center of the circular staple pattern. In this manner, each "C" shaped staple (1790) overlaps adjacent staples (1790) with the resultant staple pattern eliminating gaps in the circular staple pattern.

FIG. 31 illustrates a relaxed state of the nested arrangement of staples (1790); however, the nested arrangement of staples (1790) allows for expansion of the staple line in response to tissue expansion forces acting on staples (1790). More specifically, as tissue forces act on staples (1790) in their nested arrangement, staples (1790) reorient their relative position such that the nesting arrangement becomes less such that the overlapping of staples (1790) decreases when the pattern expands. Furthermore, in some versions, staples (1790) can also provide for expansion by staples (1790) themselves expanding in similar ways as described above where the "C" shaped crowns (1796) adopt a less curvature shape thereby also increasing their width as described above with respect to other staple versions. In this manner, expansion of the staple line creating the anastomosis using the arrangement shown in FIG. 31 can be achieved in two ways: by the nesting pattern expanding, and/or by staples (1790) themselves expanding.

III. Exemplary Combinations

The following examples relate to various non-exhaustive ways in which the teachings herein may be combined or applied. The following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus for creating an anastomosis between two lumens, comprising: (a) a body; (b) a shaft extending distally from the body; (c) a stapling head assembly positioned at a distal end of the shaft, wherein the stapling head assembly includes: (i) an annular deck member, wherein the annular deck member includes: (A) a deck surface configured to contact a tissue defining a select one of the two lumens, (B) an annular array of staple openings formed through the deck surface, and (C) a plurality of staples configured to travel through the staple openings, each staple of the plurality of staples comprising a crown and a pair of legs extending from the crown, wherein the plurality of staples is expandable having a first configuration and a second configuration, wherein in the second configuration a distance between the pair of legs is greater than in the first configuration; (ii) a staple driver operable to drive the plurality of staples through the annular array of staple openings; and (d) an anvil configured to deform the staples driven by the staple driver to form a ring-shaped staple pattern configured to connect the two lumens.

Example 2

The apparatus of Example 1, wherein each staple of the plurality of staples comprises an angled crown such that each staple defines a "V" shape when viewed from a top or a bottom.

Example 3

The apparatus of any one or more of Example 1 through Example 2, wherein the crown comprises a weakened portion to promote bending for expandability when the staple is exposed to tension due to tissue forces.

Example 4

The apparatus of Example 3, wherein the weakened portion comprises a reduction in material of the crown.

Example 5

The apparatus of Example 4, wherein the reduction in material of the crown consists of a select one of a notch in the crown, a portion having a reduced diameter, a portion having a flat area that connects with remaining portions of the crown that are cylindrically shaped, and combinations thereof.

Example 6

The apparatus of any one or more of Example 1 through Example 5, wherein the crown of each staple of the plurality of staples comprises a spring feature comprising a bend in the crown configured to straighten, wherein the spring feature provides for automatic expansion of each of the staples after the staples are deployed.

Example 7

The apparatus of any one or more of Example 1 through Example 6, wherein the crown of each staple of the plurality of staples comprises a coil feature formed within the crown.

Example 8

The apparatus of any one or more of Example 1 through Example 7, wherein the crown of each staple of the plurality of staples comprises a hinge feature, wherein the hinge feature promotes adjustment of the staple for expandability when the staple is exposed to tension due to tissue forces.

Example 9

The apparatus of Example 8, wherein the hinge feature consists of a select one of an eyelet connected with two straight portions of the crown, and a pair of eyelets spaced apart and connected by a connecting member, wherein each eyelet of the pair of eyelets connects with a separate straight portion of the crown.

Example 10

The apparatus of any one or more of Example 1 through Example 9, wherein each staple of the plurality of staples comprises a flexible cable connecting portions of the crown.

Example 11

The apparatus of any one or more of Example 1 through Example 10, wherein the crown of each staple of the plurality of staples comprises a first portion connected with a first leg of the pair of the legs, and a second portion connected with a second leg of the pair of legs, wherein the first and the second portions are slidable relative to one another to promotes adjustment of the staple for expandability when the staple is exposed to tension due to tissue forces.

Example 12

The apparatus of any one or more of Example 1 and Example 3 through Example 11, wherein the crown of each staple of the plurality of staples comprises at least one curved portion configured to elongate when the staple is exposed to tension due to tissue forces.

Example 13

The apparatus of any one or more of Example 1 and Example 3 through Example 12, wherein the crown of each staple of the plurality of staples comprises an "S" shape.

Example 14

The apparatus of any one or more of Example 1 and Example 3 through Example 12, wherein the crown of each staple of the plurality of staples comprises a double "S" shape.

Example 15

The apparatus of any one or more of Example 1 through Example 14, wherein the annular array of staple openings is configured with a pattern having a row of nested openings such that the first configuration of the plurality of staples comprises the ring-like staple pattern with an initial nested configuration, and the second configuration of the plurality of staples comprises the ring-like staple pattern with an expanded nested configuration compared to the initial nested configuration.

Example 16

The apparatus of Example 12, wherein the at least one curved portion comprises a first end and a second end, wherein the crown of each staple comprises a pair of straight portions having a third end and a fourth end, wherein a third end of each straight portion connects with a respective one of the pair of legs of the staple, and wherein a fourth end of each straight portion connects with a respective first end and second end of the at least one curved portion.

Example 17

The apparatus of Example 16, wherein the pair of straight portions of the crown are coaxial.

Example 18

The apparatus of Example 16, wherein the pair of straight portions of the crown are non-coaxial such that the pair of straight portions are offset from one another.

Example 19

A staple for use with a stapler to create an anastomosis between two lumens, the staple comprises a crown and a pair of legs extending from the crown, wherein the staple is expandable having a first configuration and a second configuration, wherein in the second configuration a distance between the pair of legs is greater than in the first configuration, and wherein the staple transitions from the first configuration to the second configuration in response to either a release of pre-formed tension or a force imparted on the staple by tissue expansion.

Example 20

An apparatus for creating an anastomosis between two lumens, comprising: (a) a body; (b) a shaft extending distally from the body; (c) a stapling head assembly positioned at a distal end of the shaft, wherein the stapling head assembly includes: (i) an annular deck member, wherein the annular deck member includes: (A) a deck surface configured to contact a tissue defining a select one of the two lumens, (B) an annular array of staple openings formed through the deck surface, wherein the annular array of staple openings is configured with a pattern having two rows of offset opposing openings, and (C) a plurality of staples configured to travel through the staple openings, each staple of the plurality of staples comprising a crown and a pair of legs extending from the crown, wherein the plurality of staples is expandable having a first configuration and a second configuration, wherein in the second configuration a distance between the pair of legs is greater than in the first configuration; (ii) a staple driver operable to drive the plurality of staples through the annular array of staple openings; and (d) an anvil configured to deform the staples driven by the staple driver to form a ring-shaped staple pattern configured to connect the two lumens.

Example 21

The apparatus of Example 1, wherein the crown of each staple of the plurality of staples comprises a curved portion defining a "C" shape that is configured to elongate when the staple is exposed to tension due to tissue forces.

Example 22

The apparatus of any one or more of Example 1 through Example 2, wherein the annular array of staple openings is configured with a pattern having a row of nested openings such that the first configuration of the plurality of staples comprises the ring-like staple pattern with an initial nested configuration, and the second configuration of the plurality of staples comprises the ring-like staple pattern with an expanded nested configuration compared to the initial nested configuration.

IV. Miscellaneous

It should also be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Additionally, any one or more of the teachings herein may be combined with any one or more of the teachings of U.S. patent application Ser. No. 17/401,391, entitled "Methods of Forming an Anastomosis Between Organs with an Expandable Staple Pattern," filed on Aug. 13, 2021, published as U.S. Pub. No. 2023/0051305 on Feb. 16, 2023; U.S. patent application Ser. No. 17/401,428, entitled "Staple Forming Features for Circular Surgical Stapler," filed on Aug. 13, 2021, published as U.S. Pub. No. 2023/0047471 on Feb. 16, 2023; U.S. patent application No. 17/401,430, entitled "Non-Circular End Effector Features for Circular Surgical Stapler," filed on Aug. 13, 2021, published as U.S. Pub. No. 2023/0045940 on Feb. 16, 2023; U.S. patent application Ser. No. 17/401,439, entitled "Circular Surgical Stapler End Effector Having Staple Line Alignment Feature," filed on Aug. 13, 2021, published as U.S. Pub. No. 2023/0049352 on Feb. 16, 2023; U.S. patent application Ser. No. 17/401,444, entitled "Circular Surgical Stapler for Forming Pattern of Non-Tangential Staples," filed on Aug. 13, 2021, issued as U.S. Pat. No. 11,653,926 on May 23, 2023; and U.S. patent application Ser. No. 17/401,460, entitled "Circular Surgical Stapler for Forming Cross-Pattern of Staples," filed on Aug. 13, 2021, issued as U.S. Pat. No. 11,666,339 on Jun. 6, 2023. The disclosure of each of these US patent documents is incorporated by reference herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, California.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus for creating an anastomosis between two lumens, comprising:
   (a) a body;
   (b) a shaft extending distally from the body;
   (c) a stapling head assembly positioned at a distal end of the shaft, wherein the stapling head assembly includes:
      (i) an annular deck member, wherein the annular deck member includes:
         (A) a deck surface configured to contact a tissue defining a select one of the two lumens,
         (B) an annular array of staple openings formed through the deck surface, and
         (C) a plurality of staples configured to travel through the staple openings, each staple of the plurality of staples comprising a crown having a pair of straight portions and an angled central portion that interconnects inner ends of the straight portions such that the straight portions extend angularly relative to one another, and a pair of legs extending from outer ends of the straight portions of the crown, wherein each staple is expandable between a first configuration and a second configuration, wherein in the second configuration a distance between the pair of legs is greater than in the first configuration;
      (ii) a staple driver operable to drive the plurality of staples through the annular array of staple openings; and
   (d) an anvil configured to deform the staples driven by the staple driver to form a ring-shaped staple pattern configured to connect the two lumens.

2. The apparatus of claim 1, wherein each staple of the plurality of staples comprises an angled crown such that each staple defines a single "V" shape when viewed from a top or a bottom.

3. The apparatus of claim 2, wherein the annular array of staple openings is configured with a pattern having a row of nested openings such that the first configuration of the plurality of staples comprises the ring-like staple pattern with an initial nested configuration, and the second configuration of the plurality of staples comprises the ring-like staple pattern with an expanded nested configuration compared to the initial nested configuration.

4. The apparatus of claim 1, wherein the angled central portion of the crown comprises a weakened portion configured to promote bending of the crown at its midpoint for expandability when the staple is exposed to tension due to tissue forces.

5. The apparatus of claim 4, wherein the weakened portion comprises a reduction in material of the crown.

6. The apparatus of claim 5, wherein the reduction in material of the crown consists of a notch in the crown that connects with remaining portions of the crown that are cylindrically shaped.

7. The apparatus of claim 5, wherein the reduction in material of the crown consists of a portion having a reduced diameter that connects with remaining portions of the crown that are cylindrically shaped.

8. The apparatus of claim 5, wherein the reduction in material of the crown consists of a portion having a flat area that connects with remaining portions of the crown that are cylindrically shaped.

9. The apparatus of claim 1, wherein the crown of each staple of the plurality of staples comprises a spring feature comprising a bend in the crown configured to straighten, wherein the spring feature provides for automatic expansion of each of the staples after the staples are deployed.

10. The apparatus of claim 1, wherein the crown of each staple of the plurality of staples comprises a coil feature formed within the crown.

11. The apparatus of claim 1, wherein the crown of each staple of the plurality of staples comprises a hinge feature, wherein the hinge feature promotes adjustment of the staple for expandability when the staple is exposed to tension due to tissue forces.

12. The apparatus of claim 1, wherein the crown of each staple of the plurality of staples comprises a curved portion defining a "C" shape that is configured to elongate when the staple is exposed to tension due to tissue forces.

13. The apparatus of claim 1, wherein the legs of each staple in an unformed state define a first plane, wherein the straight portions of the crown of each staple in the unformed state are angled relative to one another in a second plane perpendicular to the first plane.

14. A staple for use with a stapler to create an anastomosis between two lumens, wherein the staple comprises:
 (a) a crown including a pair of straight portions that interconnect at a midpoint of the crown and are angled relative to one another; and
 (b) a pair of legs extending from the straight portions of the crown,
 wherein the staple is expandable between a first configuration and a second configuration, wherein in the second configuration a distance between the pair of legs is greater than in the first configuration.

15. The staple of claim 14, wherein the staple is configured to transition from the first configuration to the second configuration in response to a release of pre-formed tension.

16. The staple of claim 14, wherein the staple is configured to transition from the first configuration to the second configuration in response to a force imparted on the staple by tissue expansion.

17. The staple of claim 14, wherein the crown further includes a central weakened portion that interconnects the straight portions of the crown, wherein the central weakened portion is configured to promote bending of the crown at the central weakened portion for expandability when the staple is exposed to tension due to tissue forces.

18. The apparatus of claim 17, wherein the central weakened portion comprises a reduction in material of the crown.

19. An apparatus for creating an anastomosis between two lumens, comprising:
 (a) a body;
 (b) a shaft extending distally from the body;
 (c) a stapling head assembly positioned at a distal end of the shaft, wherein the stapling head assembly includes:
  (i) an annular deck member, wherein the annular deck member includes:
   (A) a deck surface configured to contact a tissue defining a select one of the two lumens,
   (B) an annular array of staple openings formed through the deck surface, wherein the annular array of staple openings is configured with a pattern having two rows of offset opposing openings, and
   (C) a plurality of staples configured to travel through the staple openings, each staple of the plurality of staples comprising a crown having a pair of straight portions and a pair of legs extending from the straight portions of the crown, wherein the straight portions are interconnected and angled relative to another to provide the crown with a single-V shape, wherein each staple is expandable between a first configuration and a second configuration, wherein in the second configuration a distance between the pair of legs is greater than in the first configuration;
  (ii) a staple driver operable to drive the plurality of staples through the annular array of staple openings; and
 (d) an anvil configured to deform the staples driven by the staple driver to form a ring-shaped staple pattern configured to connect the two lumens.

* * * * *